(12) United States Patent
Tsiagbe et al.

(10) Patent No.: US 10,370,417 B2
(45) Date of Patent: Aug. 6, 2019

(54) METHODS FOR THE DIAGNOSIS OF CANCER THROUGH DETECTION OF HUMAN ENDOGENOUS RETROVIRUS WL (HERV-WL) ENVELOPE EXPRESSION

(71) Applicant: Rutgers, The State University of New Jersey, New Brunswick, NJ (US)

(72) Inventors: Vincent K. Tsiagbe, New Rochelle, NY (US); Yu Li, Jersey City, NJ (US)

(73) Assignee: RUTGERS, THE STATE UNIVERSITY OF NEW JERSEY, New Brunswick, NJ (US)

( * ) Notice: Subject to any disclaimer, the term of this patent is extended or adjusted under 35 U.S.C. 154(b) by 16 days.

(21) Appl. No.: 15/495,627

(22) Filed: Apr. 24, 2017

(65) Prior Publication Data

US 2017/0334952 A1   Nov. 23, 2017

Related U.S. Application Data

(63) Continuation-in-part of application No. 14/198,201, filed on Mar. 5, 2014, now abandoned, which is a continuation of application No. 14/001,304, filed as application No. PCT/US2012/027289 on Mar. 1, 2012, now abandoned.

(60) Provisional application No. 61/447,750, filed on Mar. 1, 2011.

(51) Int. Cl.
| | |
|---|---|
| G01N 33/574 | (2006.01) |
| C07K 14/15 | (2006.01) |
| C07K 16/10 | (2006.01) |
| C12Q 1/68 | (2018.01) |
| C12Q 1/70 | (2006.01) |
| C07K 7/08 | (2006.01) |
| C07K 14/005 | (2006.01) |
| A61K 38/00 | (2006.01) |
| C07K 16/30 | (2006.01) |

(52) U.S. Cl.
CPC ............... *C07K 14/15* (2013.01); *C07K 7/08* (2013.01); *C07K 14/005* (2013.01); *C07K 16/1036* (2013.01); *C07K 16/1063* (2013.01); *C12Q 1/68* (2013.01); *C12Q 1/702* (2013.01); *G01N 33/574* (2013.01); *G01N 33/57407* (2013.01); *G01N 33/57426* (2013.01); *A61K 38/00* (2013.01); *C07K 16/30* (2013.01); *C07K 2317/34* (2013.01); *C07K 2317/55* (2013.01); *C12N 2710/14143* (2013.01); *C12N 2740/10022* (2013.01); *C12N 2740/13022* (2013.01); *G01N 2333/15* (2013.01)

(58) Field of Classification Search
CPC ................. C07K 7/08; C07K 16/1036; G01N 33/57407; C12N 2740/10022
See application file for complete search history.

(56) References Cited

U.S. PATENT DOCUMENTS

| | | |
|---|---|---|
| 7,666,420 B2 | 2/2010 | Marche et al. |
| 2005/0196754 A1 | 9/2005 | Drmanac et al. |
| 2010/0074894 A1 | 3/2010 | Perron |

OTHER PUBLICATIONS

Grandi, N., and E. Tramontano, 2018, HERV Envelope Proteins: Physiological Role and Pathogenic Potential in Cancer and Autoimmunity, Front. Microbiol. 9(article 462):1-26.*
Januszkiewicz-Lewandowska, D., et al., 2013, Env Gene Expression of Human Endogenous Retrovirus-K and Human Endogenous Retrovirus-W in Childhood Acute Leukemia Cells, Acta. Haematol. 129:232-237.*
Kim, H.-S., et al., 2008, Quantitative Expression of the HERV-W env Gene in Human Tissues, Arch. Virol. 153:1587-1591.*
Strongin, W., 1992, Sensitivity, Specificity, and Predictive Value of Diagnostic Tests: Definitions and Clinical Applications, in Laboratory Diagnosis of Viral Infections, Lennette, E. H., ed. Marcel Dekker, Inc., NY, NY, pp. 211-219.*
Strongin, W., 1992, Sensitivity, specificity and predictive value of diagnostic tests: definitions and clinical applications, in Laboratory Diagnosiss of Viral Infections, Lennette, E., H., ed. Marcel Dekker, Inc, NY, NY, pp. 211-219.*
Mardsen et al. "Short Communication: Activating Stimuli Enhance Immunotoxin-mediated Killing of HIV-infected Macrophages." AIDS Res. Hum. Retroviruses 24(11): 1399-1404. (2008).
Brudek et al: "B Cells and Monocytes from Patients with Active Multiple Sclerosis Exhibit Increased Surface Expression of Both HERV-H Env and HERV-W Env, Accompanied by Increased Seroreactivity", Nov. 16, 2009, Retrovirology, vol. 6, No. 104, pp. 1-13.

* cited by examiner

*Primary Examiner* — Jeffrey S Parkin
(74) *Attorney, Agent, or Firm* — Fox Rothschild LLP

(57) ABSTRACT

The present invention relates to methods and kits for diagnosis of cancer in a subject by detecting human endogenous retrovirus env (HERV-WL) polypeptides.

9 Claims, 14 Drawing Sheets
Specification includes a Sequence Listing.

Fig. 6A

Predicted Amino-acid translations of HERV-WL *env*

Frame 1:

```
  1 atggccctcccttatcatattttctctttactgttctcttaccc
    M  A  L  P  Y  H  I  F  L  F  T  V  L  L  P
 46 cctttcattctcactgcaccccctccatgccactgtatgaccagt
    P  F  I  L  T  A  P  P  P  C  H  C  M  T  S
 91 agctcccgttaccaagagtttctatggagaatgcggcttcccgga
    S  S  R  Y  Q  E  F  L  W  R  M  R  L  P  G
136 aatattgatgccccatcatataggagtttatctaagggaaacccc
    N  I  D  A  P  S  Y  R  S  L  S  K  G  N  P
181 accttcactgcccatacccatatgccccgcaactgctgtaactct
    T  F  T  A  H  T  H  M  P  R  N  C  C  N  S
226 gccactctttgcatgcatgcaaatactcattattggacagggaaa
    A  T  L  C  M  H  A  N  T  H  Y  W  T  G  K
271 attttaatcctagttgtccgggaggacttggagccactgtctgt
    I  F  N  P  S  C  P  G  G  L  G  A  T  V  C
316 tggacttacttcacccataccagtatgtctgatgggcgtggagtt
    W  T  Y  F  T  H  T  S  M  S  D  G  R  G  V
361 caagatcaggcaggagaaaaacacataaaggaagtaatctcccaa
    Q  D  Q  A  G  E  K  H  I  K  E  V  I  S  Q
406 ctgacccgggtacatagcacccctaaccctacaaaggactagat
    L  T  R  V  H  S  T  P  N  P  Y  K  G  L  D
451 ctctcaaaactacatgaaaccctccatacccatactcaccaggta
    L  S  K  L  H  E  T  L  H  T  H  Q  V
496 agcctatttaataccaccctcactgggctccatgaggccttggcc
    S  L  F  N  T  T  L  T  G  L  H  E  A  L  A
541 caaaaccctactaactgttga 561
    Q  N  P  T  N  C  *
```

Fig. 6B

Frame 2:
```
 562 atgtgcctcccccctgcactacaggccacatatttcaatccctgta
      M  C  L  P  L  H  Y  R  P  H  I  S  I  P  V
 607 cctgaacaatggaacaacttcagcacagaaataaacaccacttcc
      P  E  Q  W  N  N  F  S  T  E  I  N  T  T  S
 652 attttagtaggacctcttgtttccaatctggaaataacccatacc
      I  L  V  G  P  L  V  S  N  L  E  I  T  H  T
 697 tcaaacctcgcccgtgtaaaatttagcaatactatagacacaacc
      S  N  L  A  R  V  K  F  S  N  T  I  D  T  T
 742 aactcccagtgcatcagatgggtaactcctcccacacaaatagtc
      N  S  Q  C  I  R  W  V  T  P  P  T  Q  I  V
 787 tgcctaccctcaggaatattttttgtctgtggtacctcagcctat
      C  L  P  S  G  I  F  F  V  C  G  T  S  A  Y
 832 cactgtttgaatggcttttcggaatctatgtgcttcctctcattc
      H  C  L  N  G  F  S  E  S  M  C  F  L  S  F
 877 ttagtgcaccctatgaccatctacactgaacaagatttatacaat
      L  V  H  P  M  T  I  Y  T  E  Q  D  L  Y  N
 922 tatgtcgtacctaagccccgcaacaaaagagtacccattcttcct
      Y  V  V  P  K  P  R  N  K  R  V  P  I  L  P
 967 tttgttatccgagcaggaatgctaggcagattaggtactggcatg
      F  V  I  R  A  G  M  L  G  R  L  G  T  G  M
1012 ggcagtatcacaacctctactcagttctactacaaactatctcaa
      G  S  I  T  T  S  T  Q  F  Y  Y  K  L  S  Q
1057 gaactaaatggtgacatggaacgggttgccgactccctggtcacc
      E  L  N  G  D  M  E  R  V  A  D  S  L  V  T
1102 ttgcaagatcaacttaactccctagcagcagtagtacttcaaaat
      L  Q  D  Q  L  N  S  L  A  A  V  V  L  Q  N
1147 cgaagagctttagacttgctaactgcagaaagagggggaacctgt
      R  R  A  L  D  L  L  T  A  E  R  G  G  T  C
1192 ttatttttaggggaagaatgctgttattatgttaatcaatctgga
      L  F  L  G  E  E  C  C  Y  Y  V  N  Q  S  G
1237 atcatcactgagaaagttaaagaaattcgagatggaatacaacgc
      I  I  T  E  K  V  K  E  I  R  D  G  I  Q  R
1282 agagcatag 1290
      R  A  *
```

METHODS FOR THE DIAGNOSIS OF CANCER THROUGH DETECTION OF HUMAN ENDOGENOUS RETROVIRUS WL (HERV-WL) ENVELOPE EXPRESSION

CROSS-REFERENCE TO RELATED APPLICATION

This application is a continuation-in-part of U.S. patent application Ser. No. 14/198,201, filed Mar. 4, 2014, which is a continuation of U.S. patent application Ser. No. 14/001,304, filed Aug. 23, 2013, now abandoned, which is the U.S. National Phase of International Patent Application Serial No. PCT/US12/27289, filed Mar. 1, 2012, which claims the benefit of U.S. Provisional Patent Application Ser. No. 61/447,750, filed Mar. 1, 2011, the disclosures of all of which are incorporated herein by reference in their entireties.

BACKGROUND OF THE INVENTION

About 8% of the human genome consists of sequences classified as Human endogenous retroviruses (HERVs), which are remnants of ancient retroviral integrations in the human genome. HERV elements have degenerated over millions of years of evolution and most of them can no longer encode complete proteins, let alone produce infectious viral particles, due to the accumulation of mutations, deletions, and/or truncations. Despite the fact that HERVs had integrated into the human genome millions of year ago, some HERV genes still have open reading frames (ORFs) and thus can potentially code for protein.

HERV-W expression has been detected in lung, gastric, ovarian and bladder cancers, and HERV-W has been reported to induce Vβ16 biased T cell response when presented as "multiple sclerosis retroviral particles." These observations are in line with previous findings on a mouse model for germinal center (GC)-derived B cell lymphomas. In this SJL mouse model, the lymphomas arise as a result of transcription of a retroviral superantigen (vSAg29) encoded for by an endogenous mouse mammary tumor virus (mtv29). The vSAg29 vigorously stimulates TCR Vβ16+ CD4+ T cells, which in turn elaborate copious amounts of growth-promoting cytokines upon which the lymphoma cells depend for their growth. This phenomenon has been characterized as reverse immune surveillance.

Furthermore, an examination of CD4 T cells obtained from diffuse large B cell lymphomas (DLCL), representing a major class of non-Hodgkin's lymphomas, revealed the presence of oligoclonal TCR BV families based on their non-Gaussian distribution of CDR3 lengths, when compared to normal lymph node CD4 T cells. In addition, the representation of the TCRBV families among the CD4+ T cells was skewed. One clear example is a case in which such CD4 T cells were followed in two stages of lymphoma development in a patient. Lymphoma-host CD4 T cell interaction was observed in which the lymphoma cells stimulated syngeneic response in PBL CD4 T cells, resulting in BV23 oligoclonality (92% of BV23 had the same CDR3 length as observed for the lymphoma-containing CD4 T cells).

Human cancers are a significant health problem in the United States and throughout the world. Although advances have been made in detection and treatment of the disease, there remains a need for additional means of detection and treatment of cancer.

SUMMARY OF THE INVENTION

The invention generally relates to human endogenous retrovirus env (HERV-WL) polypeptides, nucleotide sequences, HERV-WL antibodies, methods to detect cancer, and methods to determine the effectiveness of the treatment of cancer.

In one aspect, the invention provides an isolated antibody that specifically binds to a human endogenous env polypeptide (HERV-WL). In certain embodiments the antibody binds to an epitope comprising the sequence TEKVEIRDGIQRRA (SEQ ID NO:2). The antibody may be a monoclonal, polyclonal, humanized, or human antibody. The antibody may also be conjugated to a detectable label and/or a toxin.

In a second aspect, the invention provides a method of delivering a toxin to a cell that expresses HERV-WL comprising contacting a cell with an isolated antibody that specifically binds to HERV-WL, wherein the antibody is conjugated to a toxin.

In a third aspect, the invention provides a method of detecting HERV-WL in a cell comprising contacting a cell with an isolated antibody that specifically binds to HERV-WL and detecting the presence of a complex of the antibody and HERV-WL; wherein the presence of the complex is indicative of the detecting of HERV-WL in the cell. The cell may be a bone cell, muscle cell, placenta cell, endothelial cell, epithelial cell, epidermoid cell, glial cell, tumor cell, or a cancer cell. In certain embodiments, the detection is performed by immunoassay, ELISA, immunoprecipitation, immunofluorescence, immunohistochemistry, immunocytochemisty, flow cytometry, or western blot analysis.

In a fourth aspect, the invention provides a method of detecting a cancer in a subject comprising determining a level of HEVR-WL or a nucleic acid encoding HERV-WL in a biological sample from the subject; comparing the level detected in the subject's sample to a standard level in a control sample; and determining that a cancer is present if the level in the subject's sample is greater than the standard level in the control sample. In certain embodiments, the level of HERV-WL may be detected by an antibody that specifically binds to HERV-WL. In certain embodiments, the level of the nucleic acid encoding HERV-WL is determined by detecting binding of the nucleic acid to a second nucleic acid which is at least 85% identical to SEQ ID NO:1 or complement thereof, or a third nucleic acid that encodes a polypeptide that is at least 85% identical to the sequence of SEQ ID NO:2 or the complement thereof. The cancer may be a blood cancer, lymphoma, B cell lymphoma, non-Hodgkin's lymphoma, diffuse large B cell lymphoma, Burkitt's lymphoma, ameloblastoma, carcinomas including squamous cell carcinoma, mucoepidermoid carcinoma, ovarian cancer, cervical cancer, prostate cancer and breast cancer. The biological sample may be peripheral blood and/or saliva.

In a fifth aspect, the invention provides a method for determining the effectiveness of a treatment in a subject suffering from cancer comprising, obtaining a pretreatment biological sample from a subject, obtaining a post treatment biological sample from the subject, detecting the level of HERV-WL present in the samples; comparing the level of HERV-WL in the pretreatment biological sample to the post treatment biological sample, wherein the treatment is determined to be effective if the HERV-WL polypeptide present in the post-treatment biological sample is decreased compared to the HERV-WL level present in the pretreatment sample. In certain embodiments, the level of HERV-WL may be detected by an antibody that specifically binds to HERV-WL. In certain embodiments, the level of the nucleic acid encoding HERV-WL is determined by detecting binding of the nucleic acid to a second nucleic acid which is at least 85% identical to SEQ ID NO:1 or complement thereof, or a third nucleic acid that encodes a polypeptide that is at least 85% identical to the sequence of SEQ ID NO:2 or the complement thereof. The cancer may be a blood cancer, lymphoma, B cell lymphoma, non-Hodgkin's lymphoma, diffuse large B cell lymphoma, Burkitt's lymphoma, ameloblastoma, carcinomas including squamous cell carcinoma, mucoepidermoid carcinoma, ovarian cancer, cervical cancer, prostate cancer and breast cancer. The biological sample may be peripheral blood and saliva.

In a sixth aspect, the invention provides an isolated nucleic acid which is at least 85% identical to SEQ ID NO: 1. In a further embodiment, the nucleic acid hybridizes to SEQ ID NO:1 under high stringency conditions.

In a seventh aspect, the invention provides an isolated nucleic acid comprising a sequence that encodes a peptide sequence that is at least 85% identical to SEQ ID NO:2. In a further embodiment, the nucleic acid hybridizes to SEQ ID NO:2 under high stringency conditions.

In an eighth aspect, the invention provides an isolated polypeptide encoded by an isolated nucleic acid which is at least 85% identical to SEQ ID NO: 1. In a further embodiment, the polypeptide is encoded by an isolated nucleic acid that hybridizes to SEQ ID NO:1 under high stringency conditions.

In a ninth aspect, the invention provides an isolated polypeptide comprising a sequence which is as least 99% identical to SEQ ID NO:2.

In a tenth aspect, the invention provides a recombinant vector comprising an isolated nucleic acid which is at least 85% identical to SEQ ID NO: 1. The recombinant vector may comprise a nucleic acid that hybridizes to SEQ ID NO:1 under high stringency conditions. The recombinant vector may comprise a nucleic acid that hybridizes to SEQ ID NO:2 under high stringency conditions. In certain embodiments, the recombinant vector is a recombinant expression vector.

In an eleventh aspect, the invention provides an array that comprises a solid support having a plurality of locations and a nucleic acid which is at least 85% identical to SEQ ID NO: 1, a nucleic acid that hybridizes to SEQ ID NO:1 under high stringency conditions or a nucleic acid that hybridizes to SEQ ID NO:2 under high stringency conditions, attached to the locations.

In a twelfth aspect, the invention provides a host comprising a recombinant vector that contains a nucleic acid which is at least 85% identical to SEQ ID NO: 1, a nucleic acid that hybridizes to SEQ ID NO:1 under high stringency conditions or a nucleic acid that hybridizes to SEQ ID NO:2 under high stringency conditions.

In a thirteenth aspect, the invention provides a kit for performing the methods of the invention.

BRIEF DESCRIPTION OF THE DRAWINGS

FIGS. 6A and 6B is the Predicted Amino-acid translations of HERV-WL env, western blot analysis also shows two conforming major bands. FIG. 6A is Frame 1 of HERV-WL env; FIG. 6B is Frame 2 of HERV-WL env. In FIG. 6A, the nucleic acid sequence is SEQ ID NO: 13 and the amino acid sequence is SEQ ID NO: 14.

FIG. 7A depicts immune surveillance. FIG. 7B depicts reverse immune surveillance.

FIG. 10A depicts detection of HERV-WL with anti-HERV-WL polyclonal antisera. FIG. 10B depicts detection of HERV-W with commercially available anti-HERV-W polyclonal antisera. Chemiluminiscent molecular weight size markers (MW) are indicated for each blot.

DETAILED DESCRIPTION OF THE INVENTION

1. Overview

Figure 1:
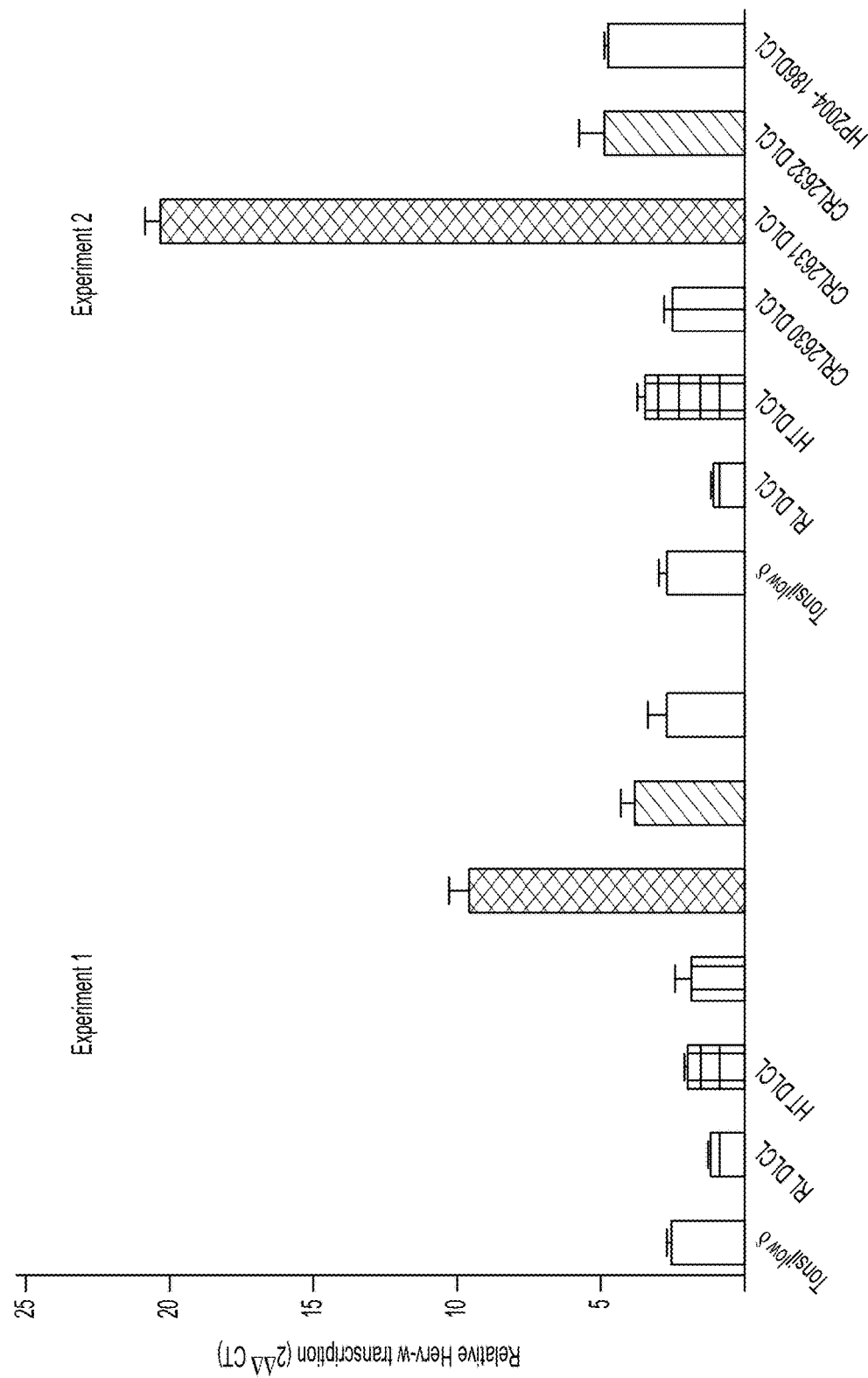
FIG. 1 illustrates the relative expression of HERV-W mRNA (normalized to that of TBP mRNA expression)±SEM in normal tonsillar low density ("activated") B cells (40/50% percol gradient interphase, Tonsil low$^\delta$) as measured by Real-Time Quantitative PCR.

This invention is based, at least in part, on unexpected discoveries of a novel human endogenous retroviral env gene, HERV-WL. Novel HERV-WL polypeptides, nucleotide sequences and HERV-WL antibodies that are useful in methods to detect cancer, and methods to determine the effectiveness of the treatment of cancer.

2. Definitions

As used herein, the singular forms "a," "an" and "the" include plural references unless the content clearly dictates otherwise.

The term "HERV-WL", as used herein, means a novel human endogenous retroviral gene that is substantially identical and complementary to SEQ ID NO:1, and refers to all isoforms and variants of a HERV-WL polypeptide and the polynucleotide that encodes the HERV-WL polypeptide.

The term "antibody" refers to an immunoglobulin or antigen-binding fragment thereof, and encompasses any such polypeptide comprising an antigen-binding fragment of an antibody. The term includes but is not limited to polyclonal, monoclonal, monospecific, polyspecific, humanized, human, single-chain, single-domain, chimeric, synthetic, recombinant, hybrid, mutated, grafted, and in vitro generated antibodies. The term "antibody" also includes antigen-binding fragments of an antibody. Examples of antigen-binding fragments include, but are not limited to, Fab fragments (consisting of the $V_L$, $V_H$, $C_L$ and $C_H1$ domains); Fd fragments (consisting of the $V_H$ and $C_H1$ domains); Fv fragments (referring to a dimer of one heavy and one light chain variable domain in tight, non-covalent association); dAb fragments (consisting of a $V_H$ domain); single domain fragments ($V_H$ domain, $V_L$ domain, $V_{HH}$ domain, or $V_{NAR}$ domain); isolated CDR regions; (Fab')$_2$ fragments, bivalent fragments (comprising two Fab fragments linked by a disulphide bridge at the hinge region), scFv (referring to a fusion of the $V_L$ and $V_H$ domains, linked together with a short linker), and other antibody fragments that retain antigen-binding function.

The term "amino" acid refers to natural and/or unnatural or synthetic amino acids, including glycine and both the D and L optical isomers, amino acid analogs (for example norleucine is an analog of leucine) and peptidomimetics.

"Animal" includes all vertebrate animals including humans. In particular, the term "vertebrate animal" includes, but not limited to, mammals, humans, canines (e.g., dogs), felines (e.g., cats); equines (e.g., horses), bovines (e.g., cattle), porcine (e.g., pigs), mice, rabbits, goats, as well as in avians. The term "avian" refers to any species or subspecies of the taxonomic class ava, such as, but not limited to, chickens (breeders, broilers and layers), turkeys, ducks, a goose, a quail, pheasants, parrots, finches, hawks, crows and ratites including ostrich, emu and cassowary.

"Array" as used herein refers to a solid support having a plurality of locations to attach a nucleotide sequence such as a probe or an antibody.

"Attached" or "immobilized' as used herein to refer to a probe or an antibody and a solid support, refers to the binding between a probe or an antibody and the solid support is sufficient to be stable under conditions of binding, washing, analysis, and removal. The binding may be covalent or non-covalent. Covalent bonds may be formed directly between the probe and the solid support or may be formed by a cross linker or by inclusion of a specific reactive group on either the solid support or the probe or both molecules. Non-covalent binding may be one or more of electrostatic, hydrophilic, and hydrophobic interactions. Included in non-covalent binding is the covalent attachment of a molecule, such as streptavidin, to the support and the non-covalent binding of a biotinylated probe to the streptavidin. Immobilization may also involve a combination of covalent and non-covalent interactions.

The "solid substrate" used for the array may be in the form of beads, particles or sheets, and may be permeable or impermeable, depending on the type of array, wherein the surface is coated with a suitable material enabling binding of the binding reagents at high affinity. For example, for linear or three-dimensional arrays the surface may be in the form of beads or particles, fibers (such as glass wool or other glass or plastic fibers) or glass or plastic capillary tubes. For two-dimensional arrays, the solid surface may be in the form of plastic, micromachined chips, membranes, slides, plates or sheets in which at least one surface is substantially flat, wherein these surfaces may comprise glass, plastic, silicon, low cross-linked and high cross-linked polystyrene, silica gel, polyamide, and the like.

"Biological sample" as used herein means a sample of biological tissue or fluid that comprises polypeptides and/or nucleic acids. Such samples include, but are not limited to, tissue isolated from animals. Biological samples may also include sections of tissues such as biopsy and autopsy samples, frozen sections taken for histologic purposes, blood, plasma, serum, sputum, saliva, stool, tears, mucus, hair, and skin. Biological samples also include explants and primary and/or transformed cell cultures derived from patient tissues. A biological sample may be provided by removing a sample of cells from an animal, but can also be accomplished by using previously isolated cells (e.g., isolated by another person, at another time, and/or for another purpose), or by performing the methods of the invention in vivo.

As used herein, the terms "biopsy" and "biopsy tissue" refer to a sample of tissue or fluid that is removed from a subject for the purpose of determining if the sample contains cancerous tissue. In some embodiments, biopsy tissue or fluid is obtained because a subject is suspected of having cancer, and the biopsy tissue or fluid is then examined for the presence or absence of cancer.

The terms "cancer cell" and "tumor cell", and grammatical equivalents refer to the total population of cells derived from a tumor, a cancer or a pre-cancerous lesion.

"Complement" or "complementary" as used herein means Watson-Crick or Hoogsteen base pairing between nucleotides or nucleotide analogs of nucleic acid molecules.

"Conservatively modified variants" applies to both amino acid and nucleic acid sequences. "Amino acid variants" refers to amino acid sequences. With respect to particular nucleic acid sequences, conservatively modified variants refers to those nucleic acids which encode identical or essentially identical amino acid sequences, or where the nucleic acid does not encode an amino acid sequence, to essentially identical or associated (e.g., naturally contiguous) sequences. Because of the degeneracy of the genetic code, a large number of functionally identical nucleic acids encode most proteins. For instance, the codons GCA, GCC, GCG and GCU all encode the amino acid alanine. Thus, at every position where an alanine is specified by a codon, the codon can be altered to another of the corresponding codons described without altering the encoded polypeptide. Such nucleic acid variations are "silent variations", which are one species of conservatively modified variations. Every nucleic acid sequence herein which encodes a polypeptide also describes silent variations of the nucleic acid. One of skill will recognize that in certain contexts each codon in a nucleic acid (except AUG, which is ordinarily the only codon for methionine, and TGG, which is ordinarily the only codon for tryptophan) can be modified to yield a functionally identical molecule. Accordingly, silent variations of a nucleic acid which encodes a polypeptide is implicit in a described sequence with respect to the expression product.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant", including where the alteration results in the substitution of an amino acid with a chemically similar amino acid. Conservative substitution tables providing functionally similar amino acids are well known in the art. Guidance concerning which amino acid changes are likely to be phenotypically silent can also be found in Bowie et al., 1990, Science 247:1306 1310. Such conservatively modified variants are in addition to and do not exclude polymorphic variants, interspecies homologs, and alleles. Typical conservative substitutions include but are not limited to: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M) (see, e.g., Creighton, Proteins (1984)). Amino acids can be substituted based upon properties associated with side chains, for example, amino acids with polar side chains may be substituted, for example, Serine (S) and Threonine (T); amino acids based on the electrical charge of a side chains, for example, Arginine (R) and Histidine (H); and amino acids that have hydrophobic side chains, for example, Valine (V) and Leucine (L). As indicated, changes are typically of a minor nature, such as conservative amino acid substitutions that do not significantly affect the folding or activity of the protein.

The term "humanized antibody", and "engineered antibody", as used herein, is intended to include antibodies having variable region frameworks derived from sequences of human origin. Furthermore, if the antibody contains a constant region, the constant region is typically derived from such human sequences, e.g., human germline sequences, or naturally occurring (e.g., allotypes) or mutated versions of human germline sequences. The humanized antibodies of the invention may include amino acid residues not encoded by human sequences (e.g., mutations introduced by random or site-specific mutagenesis in vitro or by somatic mutation in vivo).

As used herein, the term "epitope" refers to a site on an antigen to which B and/or T cells respond or a site on a molecule against which an antibody will be produced and/or to which an antibody will bind. For example, an epitope can be recognized by an antibody defining the epitope. An epitope can be either a "linear epitope" (where a primary amino acid primary sequence comprises the epitope; typically at least 3 contiguous amino acid residues, and more usually, at least 5, and up to about 8 to about 10 amino acids in a unique sequence) or a "conformational epitope" (an epitope wherein the primary, contiguous amino acid sequence is not the sole defining component of the epitope). A conformational epitope may comprise an increased number of amino acids relative to a linear epitope, as this conformational epitope recognizes a three-dimensional structure of the peptide or protein. For example, when a protein molecule folds to form a three dimensional structure, certain amino acids and/or the polypeptide backbone forming the conformational epitope become juxtaposed enabling the antibody to recognize the epitope. Methods of determining conformation of epitopes include but are not limited to, for example, x-ray crystallography, two-dimensional nuclear magnetic resonance spectroscopy and site-directed spin labeling and electron paramagnetic resonance spectroscopy. See, for example, Epitope Mapping Protocols in Methods in Molecular Biology, Vol. 66, Glenn E. Morris, Ed. (1996), the disclosure of which is incorporated in its entirety herein by reference.

A "fusion polypeptide" refers to a polypeptide created through the joining of two or more heterologous proteins or polypeptides. A heterologous protein, polypeptide, nucleic acid, or gene is one that originates from a foreign species, or, if from the same species, is substantially modified from its original form. Two fused domains or sequences are heterologous to each other if they are not adjacent to each other in a naturally occurring protein or nucleic acid.

"Host cell" as used herein refers to a naturally occurring cell or a transformed cell that contains a vector and supports the replication of the vector. Host cells may be cultured cells, explants, cells in vivo, and the like. Host cells may be prokaryotic cells such as E. coli, or eukaryotic cells such as yeast, insect, amphibian, or mammalian cells, such as CHO, HeLa.

"Identical" or "identity" as used herein in the context of two or more nucleic acids or polypeptide sequences, means that the sequences have a specified percentage of nucleotides or amino acids that are the same over a specified region. The percentage may be calculated by comparing optimally aligning the two sequences, comparing the two sequences over the specified region, determining the number of positions at which the identical residue occurs in both sequences to yield the number of matched positions, dividing the number of matched positions by the total number of positions in the specified region, and multiplying the result by 100 to yield the percentage of sequence identity. In cases where the two sequences are of different lengths or the alignment produces staggered end and the specified region of comparison includes only a single sequence, the residues of single sequence are included in the denominator but not the numerator of the calculation. When comparing DNA and RNA, thymine (T) and uracil (U) are considered equivalent. Identity may be performed manually or by using computer sequence algorithm such as BLAST or BLAST 2.0.

"Label" as used herein may mean a composition detectable by spectroscopic, photochemical, biochemical, immunochemical, chemical, or other physical means. For example, useful labels include radioactive isotopes, fluorescent dyes, electron-dense reagents, enzymes (e.g., as commonly used in an ELISA), biotin, digoxigenin, or haptens, green fluorescent protein, and other entities which can be made detectable. A label may be incorporated into nucleic acids and proteins at any position.

As used herein, the term "linker" refers to a chemical moiety that connects a molecule to another molecule, covalently links separate parts of a molecule or separate molecules. The linker provides spacing between the two molecules or moieties such that they are able to function in their intended manner. Examples of linking groups include peptide linkers, enzyme sensitive peptide linkers/linkers, self-immolative linkers, acid sensitive linkers, multifunctional organic linking agents, bifunctional inorganic crosslinking agents and other linkers known in the art. The linker may be stable or degradable/cleavable.

As used herein, the terms "polynucleotide", "nucleotide sequence" or "nucleic acid" refer to a polymer composed of a multiplicity of nucleotide units (ribonucleotide or deoxyribonucleotide or related structural variants) linked via phosphodiester bonds, including but not limited to, DNA or RNA. The term encompasses sequences that include any of the known base analogs of DNA and RNA. Examples of a nucleic acid include and are not limited to mRNA, miRNA, tRNA, rRNA, snRNA, siRNA, dsRNA, cDNA and DNA/RNA hybrids. Nucleic acids may be single stranded or double stranded, or may contain portions of both double stranded and single stranded sequence. The nucleic acid may be DNA, both genomic and cDNA, RNA, or a hybrid, where the nucleic acid may contain combinations of deoxyribo- and ribo-nucleotides, and combinations of bases including uracil, adenine, thymine, cytosine, guanine, inosine, xanthine hypoxanthine, isocytosine and isoguanine. Nucleic acids may be obtained by chemical synthesis methods or by recombinant methods. As will be appreciated by those in the art, the depiction of a single strand also defines the sequence of the complementary strand. Thus, a nucleic acid also encompasses the complementary strand of a depicted single strand. As will also be appreciated by those in the art, many variants of a nucleic acid may be used for the same purpose as a given nucleic acid. Thus, a nucleic acid also encompasses substantially identical nucleic acids and complements thereof. As will also be appreciated by those in the art, a single strand provides a probe for a probe that may hybridize to the target sequence under stringent hybridization conditions. Thus, a nucleic acid also encompasses a probe that hybridizes under stringent hybridization conditions.

The term "in operable combination", "in operable order" or "operably linked" refers to the linkage of nucleic acid sequences in such a manner that a nucleic acid molecule capable of directing the transcription of a given gene and/or the synthesis of a desired protein molecule is produced. The term also refers to the linkage of amino acid sequences in such a manner so that a functional protein is produced.

As used herein the term "peptide" is used interchangeably with the term "polypeptide", "protein" and "amino acid sequence", in its broadest sense refers to a compound of two or more subunit amino acids, amino acid analogs or peptidomimetics.

"Probe" as used herein refers to an oligonucleotide capable of binding to a target nucleic acid of complementary sequence through one or more types of chemical bonds, usually through complementary base pairing, usually through hydrogen bond formation. Probes may bind target sequences lacking complete complementarity with the probe sequence depending upon the stringency of the hybridization conditions. There may be any number of base pair mismatches which will interfere with hybridization between the target sequence and the single stranded nucleic acids of the present invention. However, if the number of mutations is so great that no hybridization can occur under even the least stringent of hybridization conditions, the sequence is not a complementary target sequence. A probe may be single stranded or partially single and partially double stranded. The strandedness of the probe is dictated by the structure, composition, and properties of the target sequence. Probes may be directly labeled or indirectly labeled such as with biotin to which a streptavidin complex may later bind. A probe may range in length from 5 nucleotides to a 1000 nucleotides in length, most preferably from 10 to 50 nucleotides in length.

"Promoter" as used herein refers to a synthetic or naturally-derived molecule which is capable of conferring or activating expression of a nucleic acid in a cell. A promoter may comprise one or more specific regulatory elements to further enhance expression and/or to alter the spatial expression and/or temporal expression of same. A promoter may also comprise distal enhancer or repressor elements, which can be located as much as several thousand base pairs from the start site of transcription. A promoter may be derived from sources including viral, bacterial, fungal, plants, insects, and animals. A promoter may regulate the expression of a gene component constitutively, or differentially with respect to cell, the tissue or organ in which expression occurs or, with respect to the developmental stage at which expression occurs, or in response to external stimuli such as physiological stresses, pathogens, metal ions, or inducing agents. Representative examples of promoters include the bacteriophage T7 promoter, bacteriophage T3 promoter, SP6 promoter, lac operator-promoter, tac promoter, SV40 late promoter, SV40 early promoter, RSV-LTR promoter, CMV IE promoter, SV40 early promoter or SV40 late promoter and the CMV IE promoter.

A "recombinant" peptide, polypeptide, or protein refers to a peptide, polypeptide, or protein produced by recombinant DNA techniques; i.e., produced from cells transformed by an exogenous DNA construct encoding the desired peptide, polypeptide, or protein.

The term "standard level" refers to a control level of a particular protein expressed in samples of the same type of tissue or cells from subjects who do not have cancer; for example, a predetermined standard can be a control level determined based upon the expression of the HERV-WL gene in tissue isolated from subjects who do not have breast cancer.

"Selectable marker" as used herein refers to any gene which confers a phenotype on a cell in which it is expressed to facilitate the identification and/or selection of cells which are transfected or transformed with a genetic construct. Representative examples of selectable markers include the ampicillin-resistance gene, tetracycline-resistance gene, bacterial kanamycin-resistance gene, zeocin resistance gene, the AURI-C gene which confers resistance to the antibiotic aureobasidin A, phosphinothricin-resistance gene, neomycin phosphotransferase gene (nptII), hygromycin-resistance gene, beta-glucuronidase (GUS) gene, chloramphenicol acetyltransferase (CAT) gene, green fluorescent protein-encoding gene and luciferase gene.

"Stringent hybridization conditions" as used herein refers to conditions under which a first nucleic acid sequence (e.g., probe) will hybridize to a second nucleic acid sequence (e.g., target), such as in a complex mixture of nucleic acids, but to no other sequences. Stringent conditions are sequence-dependent and will be different in different circumstances. One with ordinary skill can determine the appropriate conditions according to standard assays known in the art.

As used herein, the term "subject" refers to any animal (e.g., a mammal), including, but not limited to humans, non-human primates, rodents, and the like, which is to be the recipient of a particular treatment. Typically, the terms "subject" and "patient" are used interchangeably herein in reference to a human subject.

"Substantially complementary" as used herein refers to that a first sequence is at least 60%, 65%, 70%, 75%, 80%, 85%, 90%, 95%, 97%, 98% or 99% identical to the complement of a second sequence over a region of 8, 9, 10, 11, 12, 13, 14, 15, 16, 17, 18, 19, 20, 21, 22, 23, 24, 25, 30, 35, 40, 45, 50 or more nucleotides, or that the two sequences hybridize under stringent hybridization conditions.

"Substantially identical" as used herein refers to that a first and second sequence are at least 60%, 65%, 70%, 75%, 80%, 85%, 90%, 95%, 97%, 98% or 99% identical over a region of 8, 9, 10, 11, 12, 13, 14, 15, 16, 17, 18, 19, 20, 21, 22, 23, 24, 25, 30, 35, 40, 45, 50 or more nucleotides or amino acids, or with respect to nucleic acids, if the first sequence is substantially complementary to the complement of the second sequence.

The term "tumor" as used herein refers to any mass of tissue that results from excessive cell growth or proliferation, either benign (noncancerous) or malignant (cancerous), including pre-cancerous lesions.

"Vector" as used herein refers to a nucleic acid sequence containing an origin of replication. A vector may be a plasmid, bacteriophage, bacterial artificial chromosome, yeast artificial chromosome or a virus. A vector may be a DNA or RNA vector. A vector may be either a self-replicating extrachromosomal vector or a vector which integrates into a host genome. The term "expression vector" refers to a nucleic acid assembly containing a promoter which is capable of directing the expression of a sequence or gene of interest in a cell. Vectors typically contain nucleic acid sequences encoding selectable markers for selection of cells that have been transfected by the vector. Generally, "vector construct," "expression vector," and "gene transfer vector," refer to any nucleic acid construct capable of directing the expression of a gene of interest and which can transfer gene sequences to target cells or host cells.

3. HERV-WL Antibody

The present invention provides isolated antibodies that specifically bind to the human endogenous retrovirus env polypeptide (HERV-WL). SEQ ID NO:1 is a nucleotide sequence that encodes the HERV-WL polypeptide. The antibody of the invention, which is against HERV-WL, can be obtained by methods known in the art, for example by immunizing an animal with HERV-WL or an polypeptide selected from the amino acid sequence of HERV-WL to which an antibody of the invention specifically binds with measurable affinity, or an epitope selected within the HERV-WL polypeptide, and collecting and purifying the antibody produced in vivo according to a common procedure, known to those with skill in the art. The HERV-WL polypeptide contains a peptide region TEKVKEIRDGIQRRA (SEQ ID NO:2). Routine methods to produce HERV-WL polypeptide, a polypeptide selected from the amino acid sequence of HERV-WL to which an antibody of the invention specifically binds with measurable affinity, or a polypeptide of SEQ ID NO:2 as an epitope on an antigen are known in the art. In certain embodiments, HERV-WL polypeptide, a polypeptide selected from the amino acid sequence of HERV-WL to which an antibody of the invention specifically binds with measurable affinity, or a polypeptide of SEQ ID NO:2 can be used as an epitope on an antigen and an animal can be immunized with HERV-WL polypeptide, apolypeptide selected from the amino acid sequence of HERV-WL to which an antibody of the invention specifically binds with measurable affinity, or SEQ ID NO:2. The antigen may comprise an epitope that is substantially identical to HERV-WL polypeptide, a polypeptide selected from the amino acid sequence of HERV-WL to which an antibody of the invention specifically binds with measurable affinity, or a polypeptide of SEQ ID NO:2. The epitope may also be a conservatively modified variant of HERV-WL polypeptide, a polypeptide selected from the amino acid sequence of HERV-WL to which an antibody of the invention specifically binds with measurable affinity, or a polypeptide of SEQ ID NO:2. A monoclonal antibody can be obtained by fusing antibody-producing cells which produce an antibody against HERV-WL with myeloma cells to establish a hybridoma according to known methods (for example, Kohler and Milstein, Nature, (1975) 256, pp. 495-497; Kennet, R. ed., Monoclonal Antibodies, pp. 365-367, Plenum Press, N.Y. (1980)).

The antibody of this invention also includes humanized HERV-WL antibodies. The use of transgenic mice carrying human immunoglobulin (Ig) loci in their germline configuration provide for the isolation of high affinity fully human monoclonal antibodies directed against a variety of targets including human self antigens for which the normal human immune system is tolerant (see for example Lonberg, N. et al., U.S. Pat. Nos. 5,569,825, 6,300,129; Kucherlapati, et al., U.S. Pat. No. 6,713,610). The endogenous immunoglobulin loci in such mice can be disrupted or deleted to eliminate the capacity of the animal to produce antibodies encoded by endogenous genes.

Antibodies obtained from non-human sources can be humanized. For example, the humanized antibody can comprise portions derived from an immunoglobulin of nonhuman origin with the requisite specificity, such as a mouse, and from immunoglobulin sequences of human origin (e.g., chimeric immunoglobulin), joined together chemically by conventional techniques (e.g., synthetic) or prepared as a contiguous polypeptide using genetic engineering techniques (e.g., DNA encoding the protein portions of the chimeric antibody can be expressed to produce a contiguous polypeptide chain). Another example of a humanized immunoglobulin is one containing one or more immunoglobulin chains comprising a CDR derived from an antibody of nonhuman origin and a framework region derived from a light and/or heavy chain of human origin (e.g., CDR-grafted antibodies with or without framework changes). The framework adaptation process was based upon the similarity of framework regions between mouse mAb C836 and sequences in the human germline databases as essentially described in WO/08052108A2 "Methods For Use In Human-Adapting Monoclonal Antibodies" where framework length is matched residue for residue to the parental variable or V-regions. In total, sixteen light chain (LC) and six heavy chain (HC) frameworks were human framework adapted by combing the C836 CDRs with selected human frameworks.

Antibodies that bind to HERV-WL or an epitope selected within the HERV-WL polypeptide can be obtained using phage display technology. In a further embodiment, antibodies that bind to HERV-WL polypeptide, an arbitrary polypeptide selected from the amino acid sequence of HERV-WL, and SEQ ID NO:2 can also be obtained using phage display technology. Examples of phage display methods that can be used to make the antibodies of the present invention include those disclosed in Brinkman et al., J. Immunol. Methods 182:41-50 (1995); Ames et al., J. Immunol. Methods 184:177-186 (1995); Kettleborough et al., Eur. J. Immunol. 24:952-958 (1994). The present invention also includes nucleotide sequences that encode SEQ ID NO:2 and vectors that contain the nucleotide sequences that encode SEQ ID NO:2.

In a further embodiment, a human HERV-WL antibody is selected from a phage library, where that phage comprises human immunoglobulin genes and the library expresses human antibody binding domains as, for example, single chain antibodies (scFv), as Fab, or some other construct exhibiting paired or unpaired antibody variable regions fused to one or more of the phage coat proteins. Such phage display methods for isolating human antibodies are established in the art, see for example: U.S. Pat. Nos. 5,223,409; 5,403,484; and 5,571,698 to Ladner et al.; U.S. Pat. Nos. 5,427,908 and 5,580,717 to Dower et al.; U.S. Pat. Nos. 5,969,108 and 6,172,197 to McCafferty et al.; and U.S. Pat. Nos. 5,885,793; 6,521,404; 6,544,731; 6,555,313; 6,582,915 and 6,593,081 to Griffiths et al.

The antibodies that bind to HERV-WL and SEQ ID NO:2 may also be detectably labeled. Non-limiting examples of labels include radioactive isotopes, enzymes, enzyme fragments, enzyme substrates, enzyme inhibitors, coenzymes, catalysts, fluorophores, dyes, chemiluminescers, luminescers, or sensitizers; a non-magnetic or magnetic particle, iodinated sugars that are used as radioopaque agents, and can be appended to a linker and conjugated to the antibody. Other types of agents may be conjugated to the antibodies of this invention with or without a linker, including a toxin and/or a therapeutic agent such as small molecules that are known in the art to treat cancer, for example including without being limited, monomethyl auristatin E (MMAE), capecitabine, daunorubicin, doxorubicin, methotrexate, and Mitomycin C. An "immunotoxin" is a hybrid molecule, created by conjugating an antibody to all or part of a toxin, generally the active component of the toxin. The present invention provides an immunotoxin, an HERV-WL antibody conjugated to a toxin. Examples of toxins include without being limited, plant toxins such as arericin, saporin, and pokeweed antiviral protein (PAP), which inactivate ribosomes; and single-chain bacterial toxins such as diphtheria toxin (DT) and *Pseudomonas* exotoxin (PE). More than one agent may be conjugated to the antibody. Such methods are known to one with ordinary skill in the art, for example, BIOCONJUGATE TECHNIQUES (Academic Press; 1st edition, Greg T. Hermanson, 1996) describes techniques for modifying or crosslinking of biomolecules.

4. Methods for Detecting HERV-WL in a Cell, for the Diagnosis of Cancer, and Effectiveness of Cancer Treatment This invention also provides methods to detect HERV-WL in a cell, methods to detecting cancer in a subject and methods to assess effectiveness of a treatment in a subject suffering from cancer, as well as monitor the treatment of the cancer. A subject having cancer or prone to it can be determined based on the expression levels, patterns, or profile of the HERV-WL gene, such as nucleic acids (e.g., mRNA, miRNA) or polypeptides in a biological sample from the subject compared to a standard level in a corresponding control sample, such as a non-cancerous sample. In other words, HERV-WL polypeptides and nucleic acids can be used as markers to indicate the presence or absence of cancer or the risk of having cancer, as well as to assess the prognosis of the cancer. Diagnostic and prognostic assays of the invention include methods for assessing the expression level of the HERV-WL nucleic acids or polypeptides. An HERV-WL antibody can be used to detect the HERV-WL polypeptides. A nucleotide sequence that is substantially complementary, and/or substantially identical to HERV-WL SEQ ID NO:1 can be used to detect the expression level of HERV-WL. A nucleotide sequence that is at least 85% identical to SEQ ID NO:1 can be used to detect the expression level of HERV-WL. A nucleotide sequence that is at least 99% identical to the nucleotide sequence encoded by SEQ ID NO:2 can be used to detect the expression level of HERV-WL. Also, probes that are substantially identical or substantially complementary to SEQ ID NO:1 can be used to identify HERV-WL, as well as probes that hybridize to HERV-WL under high stringency conditions. The methods and kits herein described allow one to detect the HERV-WL in a cell, the presence of cancer in a subject and monitor the effectiveness of a cancer treatment. An increased expression or presence of HERV-WL in a biological sample from a subject compared to a standard level in a control sample may be indicative that the subject has cancer. Also a relative decrease in the expression level of HERV-WL may be indicative of the decrease in the size of a tumor or growth of a cancer, further facilitating a clinician to determine whether a cancer treatment is effective.

HERV-WL can be detected in a variety of cell types including without limitation producer cells including bone cells, muscle cells, placenta cells, endothelial cells, epithelial cells, epidermoid cells, glial cells, tumor cells, and cells derived from tumor cell lines, and cancer cells. The types of cells derived from cancers such as blood cancers, lymphoma, B cell lymphoma, non-Hodgkin's lymphoma, diffuse large B cell lymphoma, Burkitt's lymphoma, ameloblastoma, carcinomas including squamous cell carcinoma, mucoepidermoid carcinoma, ovarian cancer, cervical cancer, prostate cancer, and breast cancer.

The presence, level, or absence of the HERV-WL nucleic acid or polypeptide in a biological sample can be evaluated by obtaining a biological sample from a subject and contacting the biological sample with a compound or an agent capable of detecting the HERV-WL polypeptide or HERV-WL nucleic acid (e.g., mRNA, miRNA or genomic DNA probe). The level of expression of HERV-WL can be measured in a number of ways, including measuring the HERV-WL mRNA; or measuring the amount of HERV-WL polypeptide.

Expressed RNA samples can be isolated from biological samples using any of a number of well-known procedures. For example, biological samples can be lysed in a guanidinium-based lysis buffer, optionally containing additional components to stabilize the RNA. In some embodiments, the lysis buffer can contain purified RNAs as controls to monitor recovery and stability of RNA from cell cultures. Examples of such purified RNA templates include the Kanamycin Positive Control RNA from PROMEGA (Madison, Wis.), and 7.5 kb Poly(A)-Tailed RNA from LIFE TECHNOLOGIES (Rockville, Md.). Lysates may be used immediately or stored frozen at, e.g., −80° C.

Optionally, total RNA can be purified from cell lysates (or other types of samples) using silica-based isolation in an automation-compatible, 96-well format, such as the RNEASY purification platform (QIAGEN, Inc., Valencia, Calif.). Alternatively, RNA is isolated using solid-phase oligo-dT capture using oligo-dT bound to microbeads or cellulose columns. This method has the added advantage of isolating mRNA from genomic DNA and total RNA, and allowing transfer of the mRNA-capture medium directly into the reverse transcriptase reaction. Other RNA isolation methods are contemplated, such as extraction with silica-coated beads or guanidinium. Further methods for RNA isolation and preparation can be devised by one skilled in the art.

The methods of the present invention can also be performed using crude cell lysates, eliminating the need to isolate RNA. RNAse inhibitors are optionally added to the crude samples. When using crude cellular lysates, it should be noted that genomic DNA can contribute one or more copies of a target sequence, depending on the sample. In situations in which the target sequence is derived from one or more highly expressed genes, the signal arising from genomic DNA may not be significant. But for genes expressed at low levels, the background can be eliminated by treating the samples with DNAse, or by using primers that target splice junctions for subsequent priming of cDNA or amplification products. For example, one of the two target-specific primers could be designed to span a splice junction, thus excluding DNA as a template. As another example, the two target-specific primers can be designed to flank a splice junction, generating larger PCR products for DNA or unspliced mRNA templates as compared to processed mRNA templates. One skilled in the art could design a variety of specialized priming applications that would facilitate use of crude extracts as samples for the purposes of this invention.

The level of mRNA corresponding to HERV-WL in a cell can be determined both in situ and in vitro. Messenger RNA isolated from a biological sample can be used in hybridization or amplification assays that include, Southern or Northern analyses, PCR analyses, and probe arrays. A preferred diagnostic method for the detection of mRNA levels involves contacting the isolated mRNA with a nucleic acid probe that can hybridize to the mRNA encoded by HERV-WL. The HERV-WL probe can be a full-length nucleic acid, for example SEQ ID NO:1 or a portion thereof, for example the nucleotide sequence encoded by SEQ ID NO 2, an oligonucleotide of at least 10 nucleotides in length and sufficient to specifically hybridize under stringent conditions to the mRNA.

In one format, mRNA (or cDNA prepared from it) is immobilized on a surface and contacted with the probes, for example, by running the isolated mRNA on an agarose gel and transferring the mRNA from the gel to a membrane, such as nitrocellulose. In another format, the probes are immobilized on a solid support and the mRNA (or cDNA) is contacted with the probes, for example, in a polynucleotide chip array. A skilled artisan can adapt known mRNA detection methods for detecting the level of an mRNA.

The level of mRNA (or cDNA prepared from it) in a sample encoded by HERV-WL to be examined can be evaluated with nucleic acid amplification, e.g., by standard PCR (U.S. Pat. No. 4,683,202), RT-PCR (Bustin S. J Mol Endocrinol. 25:169-93, 2000), quantitative PCR (Ong Y. et al., Hematology. 7:59-67, 2002), real time PCR (Ginzinger D. Exp Hematol. 30:503-12, 2002), and in situ PCR (Thaker V. Methods Mol Biol. 115:379-402, 1999), or any other nucleic acid amplification method, followed by the detection of the amplified molecules using techniques known in the art.

The term "primer" refers to any nucleic acid that is capable of hybridizing at its 3' end to a complementary nucleic acid molecule, and that provides a free 3' hydroxyl terminus which can be extended by a nucleic acid polymerase. As used herein, amplification primers are a pair of nucleic acid molecules that can anneal to 5' or 3' regions of a gene (plus and minus strands, respectively, or vice-versa) and contain a short region in between. Under appropriate conditions and with appropriate reagents, such primers permit the amplification of a nucleic acid molecule having the nucleotide sequence flanked by the primers. For in situ methods, a cell or tissue sample can be prepared and immobilized on a support, such as a glass slide, and then contacted with a probe that can hybridize to mRNA. Alternative methods for amplifying nucleic acids corresponding to expressed RNA samples include those described in, e.g., U.S. Pat. No. 7,897,750.

In another embodiment, the methods of the invention further include contacting a control sample with a compound or agent capable of detecting the mRNA of HERV-WL and comparing the presence of the mRNA in the control sample with the presence of the RNA in the biological sample.

The above-described nucleic acid-based diagnostic methods can provide qualitative and quantitative information to determine whether a subject has a disease characterized by cancer or the effectiveness of a cancer treatment. An increased expression or presence of HERV-WL in a biological sample from a subject compared to a standard level in a control sample may be indicative that the subject has cancer. Also a relative decrease in the expression level of HERV-WL may be indicative of the decrease in the size of a tumor or growth of a cancer. The types of cancer include without limitation blood cancers, lymphoma, B cell lymphoma, non-Hodgkin's lymphoma, diffuse large B cell lymphoma, Burkitt's lymphoma, carcinomas, including squamous cell carcinoma and mucoepidermoid carcinoma, cervical cancer, prostate cancer, ovarian cancer and breast cancer.

A variety of methods can be used to determine the level of the HERV-WL polypeptide disclosed herein. In general, these methods include contacting an agent that selectively binds to the polypeptide, such as an antibody, to evaluate the level of polypeptide in a sample. Antibodies can be polyclonal, or monoclonal. An intact antibody, or a fragment thereof (e.g., Fab or F(ab')2) can also be used. In a preferred embodiment, the antibody bears a detectable label. The HERV-WL antibody described herein that binds to the polypeptide encoded by SEQ ID NO:1, a polypeptide selected from the amino acid sequence of HERV-WL to which an antibody of the invention specifically binds with measurable affinity, or a polypeptide of SEQ ID NO:2 is one such example. A label may be incorporated into the polpypeptide at any position. The term "labeled", with regard to the antibody, is intended to encompass direct labeling of the probe or antibody by physically linking a detectable substance to the probe or antibody, as well as indirect labeling of the antibody by reactivity with a detectable substance. For example, an antibody with a rabbit Fc region can be indirectly labeled using a second antibody directed against the rabbit Fc region, wherein the second antibody is coupled to a detectable substance. Examples of detectable substances are provided herein. Appropriate detectable substance or labels include radio isotopes (e.g., 125I, 131I, 35S, 3H, or 32P), enzymes (e.g., alkaline phosphatase, horseradish peroxidase, luciferase, or β-glactosidase), fluorescent moieties or proteins (e.g., fluorescein, rhodamine, phycoerythrin, Green Flourescent Protein (GFP), or Blue Fluorescent Protein (BFP)), or luminescent moieties (e.g., Qdot™ nanoparticles by the Quantum Dot Corporation, Palo Alto, Calif.).

The detection methods can be used to detect a polypeptide in a biological sample in vitro as well as in vivo. In vitro techniques for detection of the polypeptide include ELISAs, immunoprecipitations, immunofluorescence, immunohistochemistry; immunocytochemistry; flow cytometry; antibody arrays and Western blotting analysis. Such techniques are commonly known in the art. In vivo techniques for detection of the polypeptide include introducing into a subject a labeled HERV-WL antibody. For example, the antibody can be labeled with a detectable substance as described above. The presence and location of the detectable substance in a subject can be detected by standard imaging techniques.

An ELISA, short for Enzyme-Linked ImmunoSorbent Assay, is a biochemical technique to detect the presence of an antibody or an antigen in a sample. It utilizes a minimum of two antibodies, one of which is specific to the antigen and the other of which is coupled to an enzyme. The second antibody will cause a chromogenic or fluorogenic substrate to produce a signal. Variations of ELISA include sandwich ELISA, competitive ELISA, and ELISPOT. Because the ELISA can be performed to evaluate either the presence of antigen or the presence of antibody in a sample, it is a useful tool both for determining serum antibody concentrations and also for detecting the presence of antigen.

Immunohistochemistry and immunocytochemistry refer to the process of localizing proteins in a tissue section or cell, respectively, via the principle of antigens in tissue or cells binding to their respective antibodies. Visualization is enabled by tagging the antibody with color producing or fluorescent tags. Typical examples of color tags include, but are not limited to, horseradish peroxidase and alkaline phosphatase. Typical examples of fluorophore tags include, but are not limited to, fluorescein isothiocyanate (FITC) or phycoerythrin (PE).

Flow cytometry is a technique for counting, examining and sorting microscopic particles suspended in a stream of fluid. It allows simultaneous multiparametric analysis of the physical and/or chemical characteristics of single cells flowing through an optical/electronic detection apparatus. A beam of light (e.g., a laser) of a single frequency or color is directed onto a hydrodynamically focused stream of fluid.ID A number of detectors are aimed at the point where the stream passes through the light beam; one in line with the light beam (Forward Scatter or FSC) and several perpendicular to it (Side Scatter (SSC) and one or more fluorescent detectors). Each suspended particle passing through the beam scatters the light in some way, and fluorescent chemicals in the particle may be excited into emitting light at a lower frequency than the light source. The combination of scattered and fluorescent light is picked up by the detectors, and by analyzing fluctuations in brightness at each detector, one for each fluorescent emission peak, it is possible to deduce various facts about the physical and chemical structure of each individual particle. FSC correlates with the cell volume and SSC correlates with the density or inner complexity of the particle (e.g., shape of the nucleus, the amount and type of cytoplasmic granules or the membrane roughness).

The diagnostic methods described herein to detect HERV-WL polypeptides in a biological sample from a subject can identify subjects having, or at risk of developing cancer, or the effectiveness of cancer treatment. An increased expression or presence of HERV-WL in a biological sample from a subject compared to a standard level in a control sample may be indicative that the subject has cancer. Also a relative decrease in the expression level of HERV-WL may be indicative of the decrease in the size of a tumor or growth of a cancer. The types of cancer include without limitation blood cancers, lymphoma, B cell lymphoma, non-Hodgkin's lymphoma, diffuse large B cell lymphoma, Burkitt's lymphoma, carcinomas including squamous cell carcinoma, mucoepidermoid carcinoma, ovarian cancer, cervical cancer, prostate cancer, and breast cancer.

5. Nucleic Acid, Vector and Host Cell

The present invention provides an isolated nucleic acid comprising a nucleotide sequence referred to in SEQ ID NO:1 and the nucleotide sequence that encodes SEQ ID NO:2 or variants thereof. The variant may be a complement of the referenced nucleotide sequence. The variant may also be a nucleotide sequence that is substantially identical to the referenced nucleotide sequence or the complement thereof. The variant may also be a nucleotide sequence which hybridizes under stringent conditions to the referenced nucleotide sequence, complements thereof, or nucleotide sequences substantially identical thereto.

The nucleic acid may have a length of from 10 to 1700 nucleotides. The nucleic acid may have a length of at least 10, 11, 12, 13, 14, 15, 16, 17, 18, 19, 20, 21, 22, 23, 24, 25, 26, 27, 28, 29, 30, 35, 40, 45, 50, 60, 70, 80 or 90 nucleotides. The nucleic acid may be synthesized or expressed in a cell (in vitro or in vivo) using a vector described below. The nucleic acid may be synthesized as a single strand molecule and hybridized under stringent hybridization conditions to a substantially complementary nucleic acid to form a duplex, which is considered a nucleic acid of the invention. The nucleic acid may be introduced to a cell, tissue or organ in a single- or double-stranded form or capable of being expressed by a vector using methods well known to those skilled in the art. MOLECULAR CLONING A LABORATORY MANUAL (3rd Ed., ed. by Sambrook, Fritsch and Maniatis (Cold Spring Harbor Laboratory Press: 2001) describes commonly used techniques in molecular biology.

In particular variants of the nucleic acid, for example deletions, insertions, and/or substitutions in the sequence, which cause for so-called "silent changes", are considered to be part of the invention.

The nucleic acids of the present invention comprise also such nucleic acid sequences which contain sequences in essence equivalent to the nucleic acids described in SEQ ID NOs. 1 and 2. According to the present invention nucleic acids can show for example at least about 70%, more typically at least about 85%, 90% or 95% sequence identity to the nucleic acid sequences of SEQ ID NOs. 1 and a nucleotide sequence that encodes the polypeptide of SEQ ID NO:2.

The present invention provides a vector comprising a nucleic acid comprising a sequence which is at least 85% identical to SEQ ID NO:1. The present invention also provides a vector comprising a nucleic acid comprising a sequence that encodes a peptide sequence that is at least 85% identical to SEQ ID NO:2. The present invention also provides a vector comprising a nucleic acid which hybridizes to the nucleic acid of SEQ ID NO:1 and or a nucleotide sequence that encodes the polypeptide of SEQ ID NO:2 under high stringency conditions. An expression vector may comprise additional elements. For example, the expression vector may have two replication systems allowing it to be maintained in two organisms, e.g., in mammalian or insect cells for expression and in a prokaryotic host for cloning and amplification. For integrating expression vectors, the expression vector may contain at least one sequence homologous to the host cell genome, and preferably two homologous sequences which flank the expression construct. The integrating vector may be directed to a specific locus in the host cell by selecting the appropriate homologous sequence for inclusion in the vector. The vector may also comprise a selectable marker to allow the selection of transformed host cells.

The present invention provides a host cell comprising a vector of the invention. The cell may be a bacterial, fungal, plant, insect or animal cell. Methods are known in the art to introduce the nucleic acids of the present invention to a host cell, including electroporation and standard methods of transfection. MOLECULAR CLONING A LABORATORY MANUAL (3rd Ed., ed. by Sambrook, Fritsch and Maniatis (Cold Spring Harbor Laboratory Press: 2001) describes commonly used techniques in molecular biology.

6. Polypeptide Sequences and Fusion Polypeptides

The present invention provides an isolated polypeptide comprising a sequence encoded by SEQ ID NO:1, or having the sequence of SEQ ID NO:2 or variants thereof. According to the present invention polypeptides can show for example at least about 70%, more typically at least about 85%, 90% or 95% sequence identity to the polypeptide sequences described in SEQ ID NOs. 1 and 2.

The variants of the invention, such as the polypeptides of the present invention can be operatively linked to a polypeptide not according to the invention (e.g., heterologous amino acid sequences) to form fusion proteins. A polypeptide not according to the invention in this context refers to a polypeptide having an amino acid sequence corresponding to a polypeptide which is not substantially identical to a variant HERV-WL of the invention.

Within a fusion protein, the variant of the invention can correspond to a full length sequence. The polypeptide not according to the invention can be fused to the N-terminus or C-terminus of the variant polypeptide. For example, in one embodiment, the fusion protein is a fusion protein in which the variant sequence/s is/are fused to the C-terminus of the GST sequences. Such fusion proteins can facilitate the purification of a recombinant variant according to the invention. In another embodiment, the fusion protein is a variant of the invention containing a heterologous signal sequence at its N-terminus. In certain host cells (e.g., mammalian and yeast host cells), expression and/or secretion of a variant of the invention can be increased through use of a heterologous signal sequence.

In another example, the gp67 secretory sequence of the baculovirus envelope protein can be used as a heterologous signal sequence (Current Protocols in Molecular Biology, Ausubel et al., eds., John Wiley & Sons, 1992). Other examples of eukaryotic heterologous signal sequences include the secretory sequences of melittin and human placental alkaline phosphatase (Stratagene; La Jolla, Calif.). In yet another example, useful prokarytic heterologous signal sequences include the phoA secretory signal (Sambrook et al., supra) and the protein A secretory signal (Pharmacia Biotech; Piscataway, N.J.).

A signal sequence can be used to facilitate secretion and isolation of a variant of the invention. Signal sequences are typically characterized by a core of hydrophobic amino acids, which are generally cleaved from the mature protein during secretion in one or more cleavage events. Such signal peptides contain processing sites that allow cleavage of the signal sequence from the mature proteins as they pass through the secretory pathway. The signal sequence may direct secretion of the variant, such as from a eukaryotic host into which the expression vector is transformed, and the signal sequence may then be subsequently or concurrently cleaved. The variant of the invention may then be readily purified from the extracellular medium by known methods. Alternatively, the signal sequence can be linked to the variant of interest using a sequence, which facilitates purification, such as with a GST domain. Thus, for instance, the sequence encoding the variant of the invention may be fused to a marker sequence, such as a sequence encoding a peptide, which facilitates purification of the fused variant of the invention. In certain preferred embodiments of this aspect of the invention, the marker sequence is a hexa-histidine peptide, such as the tag provided in a pQE vector (Qiagen, Inc.), among others, many of which are commercially available. As described in Gentz et al, Proc. Natl. Acad. Sci. USA 86:821-824 (1989), for instance, hexa-histidine provides for convenient purification of the fusion protein. The HA tag is another peptide useful for purification which corresponds to an epitope derived of influenza hema-glutinin protein, which has been described by Wilson et al., Cel137:767 (1984), for instance.

7. Kits

The present invention provides a kit comprising one or more detection reagents which specifically bind to a HERV-WL polypeptide. Preferably, the kit includes an antibody that binds to the polypeptide encoded by SEQ ID NO:1 or the polypeptide of SEQ ID NO:2. The detection reagents may be peptide sequences known to flank the HERV-WL antibodies which bind to the HERV-WL polypeptides. The reagents may be bound to a solid matrix or packaged with reagents for binding them to the matrix. The solid matrix or substrate may be in the form of beads, plates, tubes, dip sticks, strips or biochips. Biochips or plates with addressable locations and discreet microtitre plates are particularly useful.

Detection reagents include wash reagents and reagents capable of detecting bound antibodies (such as labeled secondary antibodies), or reagents capable of reacting with the labeled antibody. The kit will also conveniently include a control reagent (positive and/or negative) and/or a means for detecting the antibody. Instructions for use may also be included with the kit. Most usually, the kits will be formatted for assays known in the art, for example, ELISA assays, as are known in the art.

The kit may be comprised of one or more containers and may also include collection equipment, for example, bottles, bags (such as intravenous fluids bags), vials, syringes, and test tubes. Other components may include needles, diluents and buffers. Usefully, the kit may include at least one container comprising a pharmaceutically-acceptable buffer, such as phosphate-buffered saline, Ringer's solution and dextrose solution.

The kit may be customized for use in various antibody binding assays, such as competitive binding assays, non-competitive assays, direct and indirect sandwich assays, ELISAs, fluoroimmunoassays, immunoradiometric assays, luminescence assays, chemiluminesence assays, enzyme linked immunofluorescent assays (ELIFA), immunoprecipitation assays, immunohistochemistry; immunocytochemistry; and flow cytometry. Zola, Monoclonal Antibodies: A Manual of Techniques, pp. 147-158 (CRC Press, Inc., 1987); Harlow and Lome (1998) Antibodies, A Laboratory Manual, Cold Spring Harbour Publications, New York.

The present invention provides nucleotide sequences to identify nucleotide sequences that encode the HERV-WL polypeptide in a biological sample. Such nucleotide sequences include SEQ ID NO:1 and a nucleotide sequence encoding the polypeptide of SEQ ID NO:2, and fragments thereof, and the complement of SEQ ID NO:1 and a nucleotide sequence encoding the polypeptide of SEQ ID NO:2, and fragments thereof, and sequences that hybridize to the foregoing sequences under high stringency conditions, and the primers disclosed herein. One with ordinary skill in the art using common recombinant methods can determine the nucleotide sequences to be used to detect a nucleotide that encodes the HERV-WL polypeptide.

The nucleotide sequences disclosed herein can be included in a kit to determine the presence of HERV-WL in a biological sample. Such a kit may contain a nucleic acid described herein together with any or all of the following: assay reagents, buffers, probes and/or primers, and sterile saline or another pharmaceutically acceptable emulsion and suspension base. In addition, the kit may include instructional materials containing directions (e.g., protocols) for the practice of the methods described herein. For example, the kit may be a kit for the amplification, detection, identification or quantification of a target HERV-WL mRNA sequence. To that end, the kit may contain a poly(T) primer, a forward primer, a reverse primer, and a probe.

In one example, a kit of the invention includes one or more microarray slides (or alternative microarray format) onto which a plurality of different nucleic acids (each corresponding to different regions or nucleic acid variants of HERV-WL) have been deposited. The kit can also include a plurality of labeled probes. Alternatively, the kit can include a plurality of nucleotide sequences suitable as probes and a selection of labels suitable for customizing the included nucleotide sequences, or other nucleotide sequences at the discretion of the practitioner. Commonly, at least one included nucleotide sequence corresponds to a control sequence, e.g., a "housekeeping" gene, β-actin or the like. Exemplary labels include, but are not limited to, a fluorophore, a dye, a radiolabel, an enzyme tag, that is linked to a nucleic acid primer.

In one embodiment, kits that are suitable for amplifying nucleic acid corresponding to the expressed RNA samples are provided. Such a kit includes reagents and primers suitable for use in any of the amplification methods described above. Alternatively, or additionally, the kits are suitable for amplifying a signal corresponding to hybridization between a probe and a target nucleic acid sample (e.g., deposited on a microarray).

In addition, one or more materials and/or reagents required for preparing a biological sample for HERV-WL expression analysis are optionally included in the kit. Furthermore, optionally included in the kits are one or more enzymes suitable for amplifying nucleic acids, including various polymerases (RT, Taq, etc.), one or more deoxynucleotides, and buffers to provide the necessary reaction mixture for amplification.

Typically, the kits are employed for analyzing HERV-WL expression patterns using mRNA as the starting template. The mRNA template may be presented as either total cellular RNA or isolated mRNA; both types of sample yield comparable results. In other embodiments, the methods and kits described in the present invention allow quantitation of other products of gene expression, including tRNA, rRNA, or other transcription products.

Optionally, the kits of the invention further include software to expedite the generation, analysis and/or storage of data, and to facilitate access to databases. The software includes logical instructions, instructions sets, or suitable computer programs that can be used in the collection, storage and/or analysis of the data. Comparative and relational analysis of the data is possible using the software provided.

EXAMPLES

The invention now being generally described, it will be more readily understood by reference to the following examples, which are included merely for purposes of illustration of certain aspects and embodiments of the present invention, and are not intended to limit the invention.

Real-Time (SYBR Green) Quantitative RT-PCR for HERV-W mRNA:

Total RNA was extracted from cultured cells, using Stat-60 (Tel-Test, Inc., Friendswood, Tex., USA), followed by treatment with DNaseI (Applied Biosystems/Ambion, Inc., Austin, Tex., USA). cDNA was synthesized using Superscript II reagents (Invitrogen Life Technologies, Carlsbad, Calif., USA). HERV-W-env (HERV-W) and TATA-binding protein (TBP) mRNA levels were measured in triplicate samples by real-time quantitative PCR (QPCR), with SYBR green detection on iCycler iQ (Bio-Rad, Hercules, Calif., USA). TBP was used as a "house-keeping gene" for normalization of HERV-W mRNA expression. Comparative threshold cycle (CT) was used to determine mRNA expression of HERV-W and TBP, relative to no template control. The forward and reverse (5'-3') PCR primers used for HERV-W (designed from GenBank accession # AF072506) were CTTAGTGCCCCCTATGACCA (SEQ ID NO: 3) and CGCCAATGCCAGTACCTAGT (SEQ ID NO: 4) (respectively); and the forward and reverse (5'-3') PCR primers used for TBP (designed from GenBank accession # CCDS5315.1) were AACAACAGCCTGCCACCTTACG (SEQ ID NO: 5) and GCTGCTGCCTTTGTTGCTCTTC (SEQ ID NO: 6) (respectively).

The $C_T$ value for each sample was normalized using the following formula: $\Delta C_T$=HERV-W $C_T$-TBP $C_T$. $\Delta\Delta C_T$ value for each sample was determined using the formula: $\Delta\Delta C_T$=sample $\Delta C_T$-RL DLCL $\Delta C_T$. The relative expression of HERV-W was calculated using the formula $2^{-\Delta\Delta C_T}$.

Figure 2:
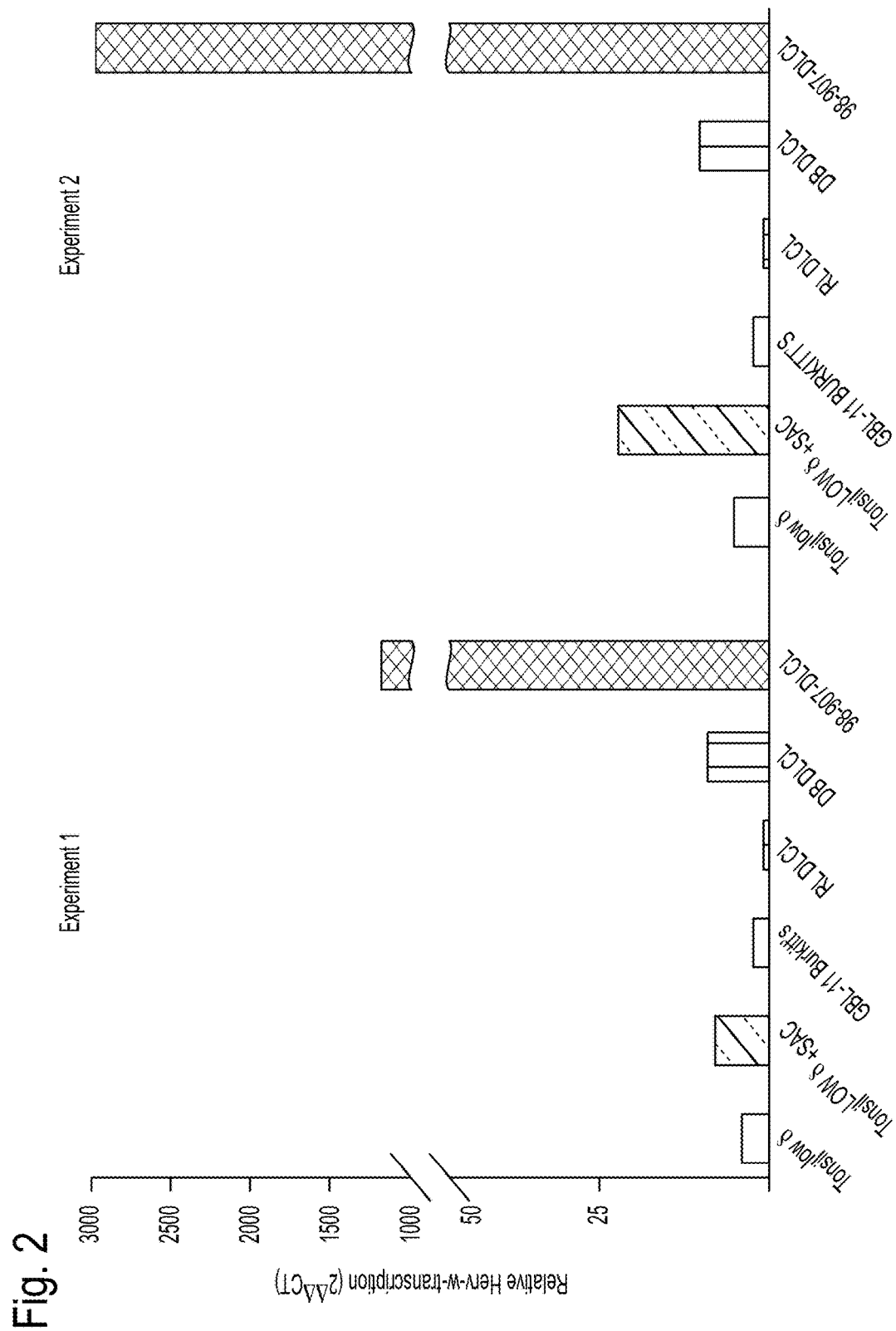
FIG. 2 illustrates the relative transcription of HERV-W in normal and lymphoma B cells as measured by Real-Time Quantitative PCR.

HERV-WL-Env Cloning and Expression:

Of a total of 8 DLCL samples examined, 5 of them expressed significantly more HERV-W than normal low density (40/50% percol gradient) S. aureus "activated" B cells from tonsil. While all the DLCL transcribe significantly more HERV-W than normal high density (50/55% percol gradient) "less-activated" B cells, CRL2631, CRL2632 and HP2004-186 transcribe significantly more HERV-W than normal "activated" B cells (of the DLCL samples shown). CRL2631 showed the highest expression of HERV-W, as shown in FIGS. 1 and 2. Diffuse large B cell lymphoma (DLCL) cells were compared in two experiments, as shown in FIG. 1. CRL2631 and CRL2632 lines, as well as fresh CD19+ purified DLCL (HP2004-186) exhibited significantly higher HERV-W mRNA expression than activated normal B cells.

The results illustrated in FIG. 2, included low density percol gradient B cells (Tonsil low$^\delta$), low density percol gradient B cells activated with a B cell mitogen (S. Aureus), Tonsil low$^\delta$+SAC), Burkitt's lymphoma line (GBL-11), DLCL lines (RL, and DB), ex vivo sample of DLCL (98-907).

Figure 9:
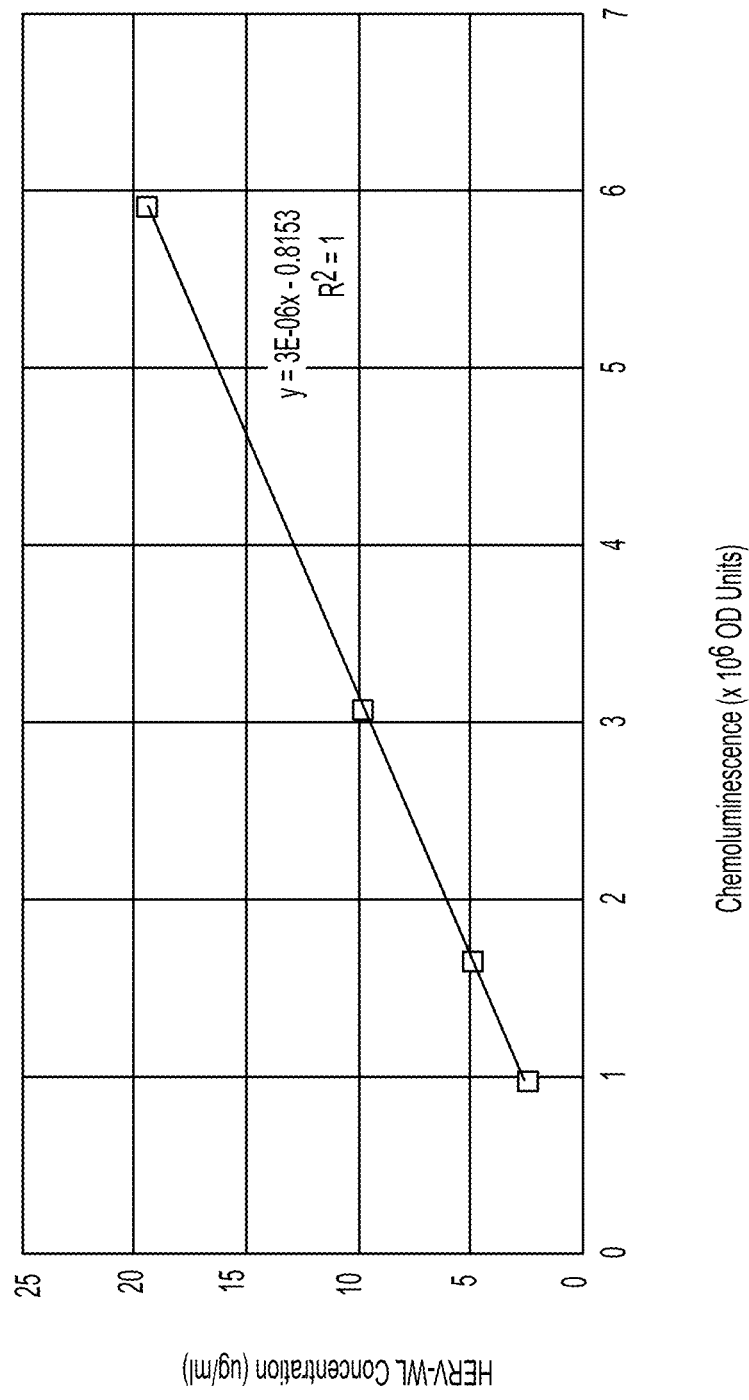
FIG. 9 depicts a standard curve of HERV-WL ELISA (polyclonal). Rabbit polyclonal anti-HERV-WL antibody was used to generate standard curve that was used to determine the concentration of HERV-WL in saliva of cancer patients and normal healthy individuals.

Human diffuse large B cell lymphoma cells, expressing high levels of human endogenous retroviral envelope protein, were used as a source to clone endogenous retroviral protein (HERV-WL). Based on the HERV-W-env mRNA expression profile in human DLCL cells that were screened, CRL2631 DLCL has the most HERV-W mRNA expression. cDNA from CRL2631 was used to amplify HERV-env full length coding sequence. The forward and reverse primers (5'-3') used were ATGGCCCTCCCTTATCAT (SEQ ID NO: 7) and CTAACTGCTTCCTGCTGA (SEQ ID NO: 8) (respectively). Easy-A high-fidelity enzyme (Stratagene, La Jolla, Calif.) was used to avoid the introduction of mutation during PCR reaction. PCR product was then cloned into TOPO TA vector (Life Technologies, Carlsbad, Calif.), clones were sequenced. One clone which had the correct insert (hereinafter named HERV-WL) was sub cloned into expression vector pDual GC (Stratagene) for bacteria expression. The sequence of the HERV-WL cloned from GC-derived B cell lymphoma was somewhat similar to the previously described syncytin-1 (HERV-W) which mediates cell—cell fusions of cytotrophoblasts into syncytiotrophoblasts. An alignment of the HERV-W sequence (positions 1044-2660, Genbank ID # NC_000007.13) and the HERV-WL (SEQ ID NO:1, FIGS. 9A and 9B) was performed, and even thought the two sequences are approximately 1.6 kb in size, there are areas of significant difference. HERV-WL had 93% nucleotide identity compared to HERV-W. HERV-WL has 2 translation frames (FIGS. 6A and 6B). HERV-WL translation frame 1 has The forward and reverse primers (5'-3') used for cloning into pDual GC were AACTCT-TCAATGGCCCTCCCTTATCAT (SEQ ID NO: 9) and CTAACTGCTTCCTGCTGA (SEQ ID NO: 10) (respectively). The plasmid used for expression in human cells was pIRES/EGFP (Stratagene); and the forward and reverse primers (5'-3') used for this cloning were TAGAATTCATG-GCCCTCCCTTATCAT (SEQ ID NO: 11) and AAGTC-GACCTAACTGCTTCCTGCTGA (SEQ ID NO: 12) (respectively). The clones of pDual GC with HERV-WL inserts were screened using the same primers used for the cloning (as stated above).

pDual GC vector has a coding sequence for his6 tag and a stop codon after the his6 tag at the 3' end of the insertion sequence. The expression vector with the correct coding sequence for HERV-WL (now referred to as pDual GC_HERV-WL_His6) was transformed into BL21 (DE3) cells, HERV-WL-His6 recombinant protein expression was induced by adding IPTG to the culture. HERV-WL-His6 recombinant protein was purified by using Ni-NTA Superflow Columns (Qiagen Valencia, Calif.). The protein was dialyzed and concentrated to 2.5 mg/ml. This protein was used to immunize rabbits and mice to produce rabbit polyclonal and mouse monoclonal antibodies, respectively. A fifteen-mer carboxyl terminal amino acid sequence (N'-TEKVKEIRDGIQRRA-C', SEQ ID NO:2) of HERV-WL was used to produce rabbit anti-peptide antibody.

Anti-HERV-WL Antibodies and Use:

Polyclonal rabbit antibodies, raised to the C-terminal peptide of HERV-WL, as well as to HERV-WL fusion protein, both detected surface expression of HERV-WL in DLCL lines and Burkitt's lymphoma cell lines. The level of surface protein expression appeared to correlate with mRNA expression.

In order to eliminate non-specific staining by the polyclonal antibodies raised to HERV-WL protein, the rabbit antibodies were purified by passing twice over pure HERV-WL affinity column. When the polyclonal anti-HERV-WL Abs were affinity purified, the detection of surface HERV-WL was greatly enhanced. The following cell lines were detected by anti-HERV-WL Abs: CRL2630, CRL2631, RL, DB, and HT are DLCL lines; Raji and Ramos are Burkitt's lymphoma cell lines; and L540 is a Hodgkin's-derived cell line.

Figure 3:
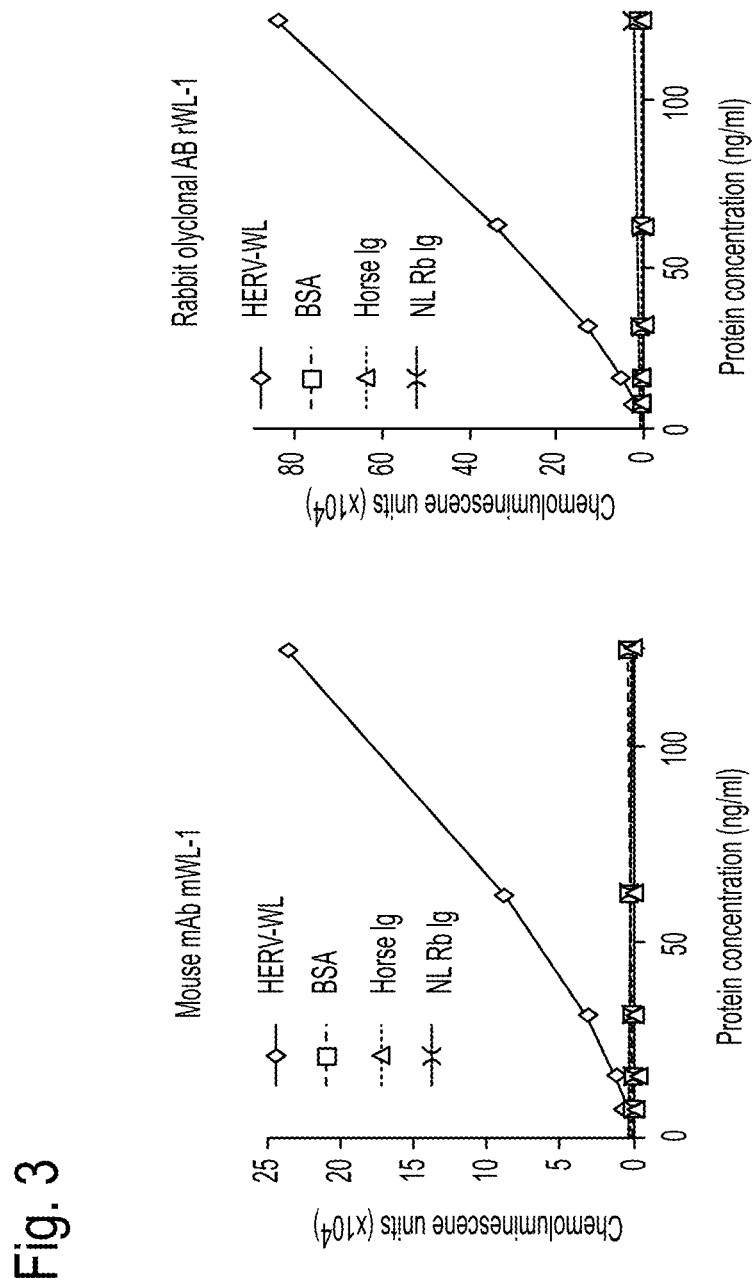
FIG. 3 depicts specificity of HERV-WL detection. ELISA plates were coated with equal concentrations of HERV-WL protein or control bovine serum Albumin (BSA), horse Ig, and normal rabbit Ig (NL RbIg).

Examination of lymphoma cell lines for surface expression of HERV-WL using mouse monoclonal anti-HERV-WL antibody indicated that HERV-WL can be detected on the surface of lymphoma cells. Mouse ascites fluid of anti-HERV-WL was used together with PE-conjugated goat anti-mouse F(ab')2 (as secondary antibody). The use of pure expressed HERV-WL protein as a blocking agent in intracellular staining of lymphoma cells showed that the mAb is, indeed, specific for HERV-WL, see FIG. 3. Furthermore, the blocking reagent was able to reduce the level of HERV-WL in lymphoma cells to that of normal human B cell. Purified IgG of anti-HERV-WL mAb was used together with PE-conjugated goat anti-mouse F(ab')2 (as secondary antibody) to detect intracellular expression of HERV-WL in DLCL lymphoma (CRL2630), compared with normal human B cells. The use of pure HERV-WL protein as a blocking reagent was able to bring down the detection of HERV-WL in lymphoma cells to a level comparable to that detected in normal B cells.

Immunohistochemistry Staining and Detection of HERV-WL in Cell Lines

To determine whether HERV-WL expression might be detected by histology in human cancer, 20 archived oral squamous cell carcinoma specimens were examined by immunohistochemistry, using affinity purified rabbit polyclonal anti-HERV-WL IgG antibody. The samples were deparaffinized, and the antigen was retrieved using 0.1M citrate buffer (pH 6.0). After peroxidase block, the slides coated with the samples were stained using biotinylated link followed by strepavidin-HRP, and hemnatoxylin counter stain. Since oral B cell lymphomas were strongly positive, the staining results were compared to human oral B-cell lymphoma tissue (as positive control) and negative controls (normal human oral mucosa with benign non-neoplastic fibroma). Staining results were evaluated independently by two previously calibrated investigators, ranking the epithelial staining according to a 0 (negative) to 3+ (intense) scale. The results were then compared.

All squamous cell carcinoma cancer samples showed diffuse positive staining with HERV-WL antibody, while most ($^{19}/_{20}$) exhibited moderate to intense immunoreactivity, see Table 1 below. Normal oral mucosa controls showed faint particulate staining limited to the basal and parabasal cell layers. Samples of B-cell lymphoma showed intense staining.

TABLE 1

Immunohistochemistry Staining of Squamous Cell Carcinoma Tissues in Comparison to Normal Epithelium (Fibroma)

| Specimen | Immunostaining |
|---|---|
| 1 | ++ |
| 2 | +++ |
| 3 | +++ |
| 4 | ++ |
| 5 | ++ |
| 6 | +++ |
| 7 | ++ |
| 8 | ++ |
| 9 | +++ |
| 10 | ++ |
| 11 | ++ |
| 12 | ++ |
| 13 | ++ |
| 14 | + |
| 15 | ++ |
| 16 | ++ |
| 17 | ++ |
| 18 | +++ |
| 19 | ++ |
| 20 | ++ |

+ = Mild staining
++ = Moderate staining
+++ = Intense staining

HERV-WL was detected in mucoepidermoid carcinoma (MEC) by immunohistochemistry staining by polyclonal anti-HERV-WL compared with fibroma (normal epithelium). Ten out of ten, mucoepidermoid carcinomas examined exhibited mild to moderate staining for HERV-WL compared to normal epidermoid cells. Minimal staining of normal epithelium is limited to the basal layer.

HERV-WL was detected in ameloblastoma by immunohistochemistry by polyclonal anti-HERV-WL staining compared with normal epithelium. Ten out of ten ameloblastoma samples showed variable expression of HERV-WL in benign ameloblastoma tumor cells, with stronger expression in the tumor periphery at the interface with the connective tissue stroma.

HERV-WL ELISA Methods and Results:

Two of three $F(ab')_2$ mouse monoclonal antibodies and one affinity purified rabbit polyclonal antibody to HERV-WL were labeled with biotin. Saliva samples were first absorbed over NeutraAvidin agarose resin to remove endogenous biotin. Both serum and saliva samples were cleared by centrifugation, prior to assay. White-walled ELISA plates were coated with serial dilutions of test samples or recombinant HERV-WL protein. Bound proteins were then coated with anti-HERV-WL antibodies. NeutraAvidin horse radish peroxidase enzyme was added. SuperSignal ELISA femto chemoluminescence substrate was used to detect target protein. Light emission was measured at 425 nm in a chemoluminometer. FIG. 6 represents the validation of HERV-WL ELISA.

Normal samples were taken from human serum (6 normal healthy individuals (hNLSRM) and one AB) and human saliva (5 normal healthy individuals). The following are the human cancer samples: human serum was taken from 2 non-Hodgkin's lymphoma patients, 2 ovarian cancer patients, 2 breast cancer patients (hNLBCSRM), 2 cervical cancer patients (hNLCCSRM), and 2 prostate cancer patients, and human saliva from 2 non-Hodgkin's lymphoma patients and 2 ovarian cancer patients.

Figure 4:
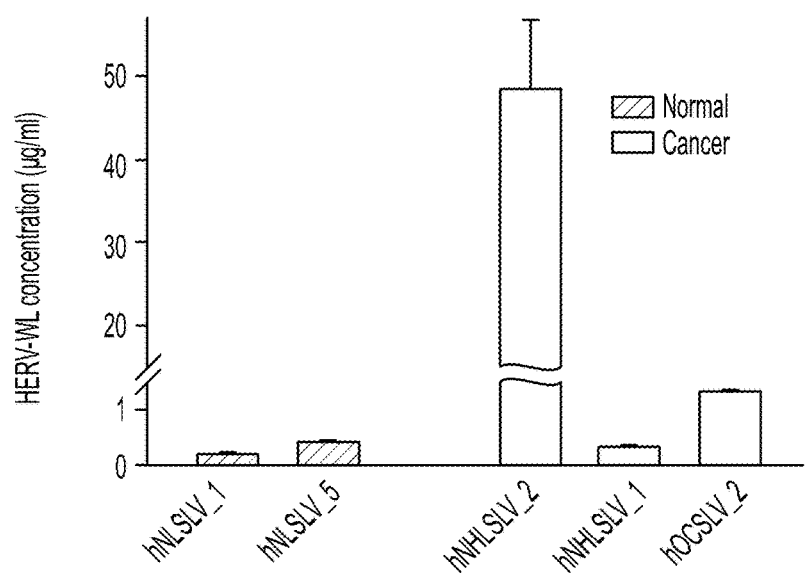
FIG. 4 depicts the detection of HERV-WL protein in serum samples from normal and cancer patients.
Figure 5:
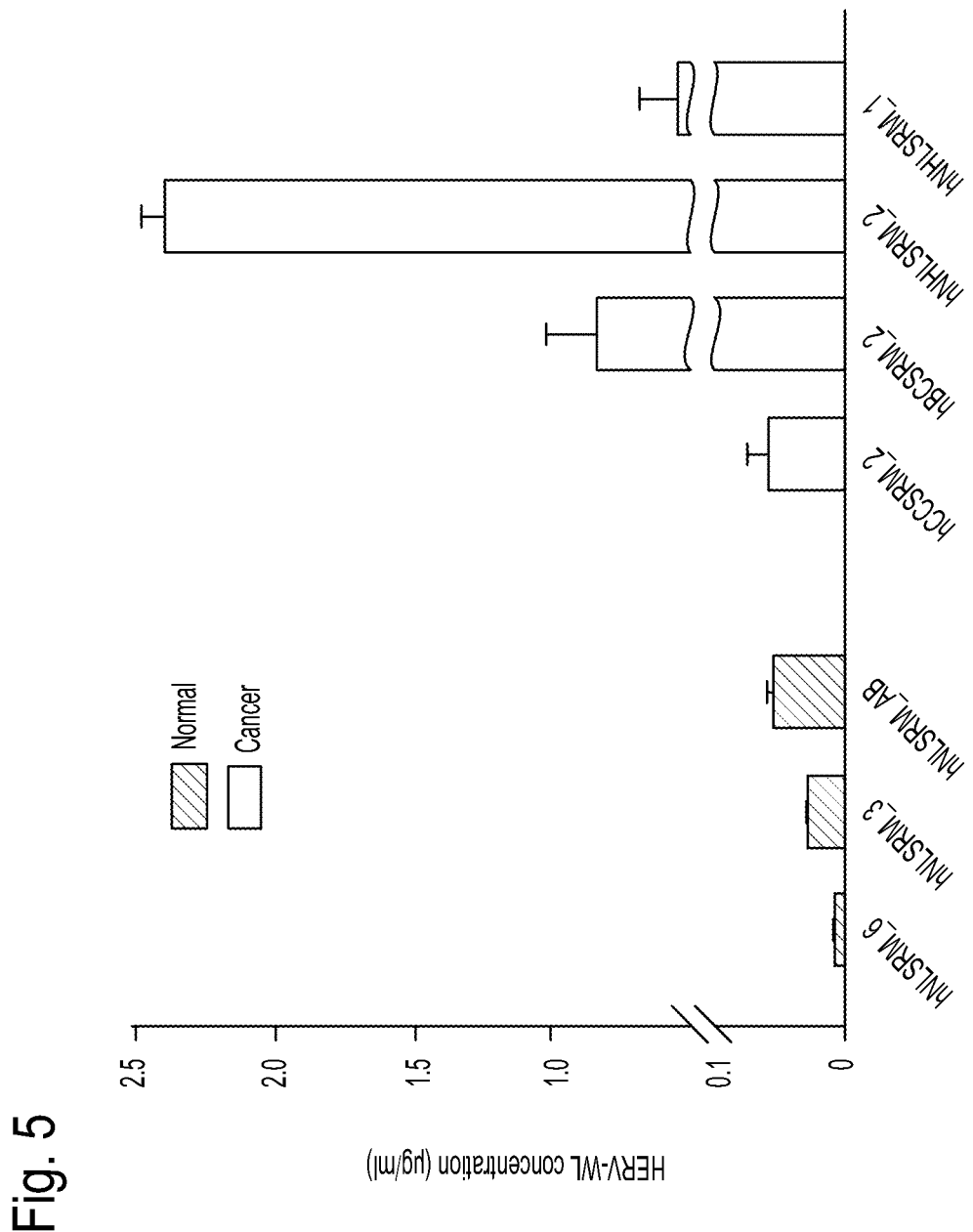
FIG. 5 depicts the detection of HERV-WL protein in saliva samples from normal and cancer patients.

HERV-WL is Increased in Ovarian Cancer, Breast Cancer and Non-Hodgkin's Lymphoma:

FIG. 4 depicts the detection of HERV-WL protein in serum samples from normal and cancer patients. The ELISA test revealed over-expression of HERV-WL in serum samples of a variety of human cancers, including no-Hodgkin's lymphoma, ovarian cancer and breast cancer. FIG. 5 depicts the detection of HERV-WL protein in saliva samples from normal and cancer patients. Three normal saliva (hNLSLV) samples and one ovarian cancer (hOCSLV) did not have detectable HERV-WL. One non-Hodgkin's Lymphoma (hNHSLV2) had extremely high levels of HERV-WL. Values represent means (±SEM) of triplicate determinations.

Figure 7A:
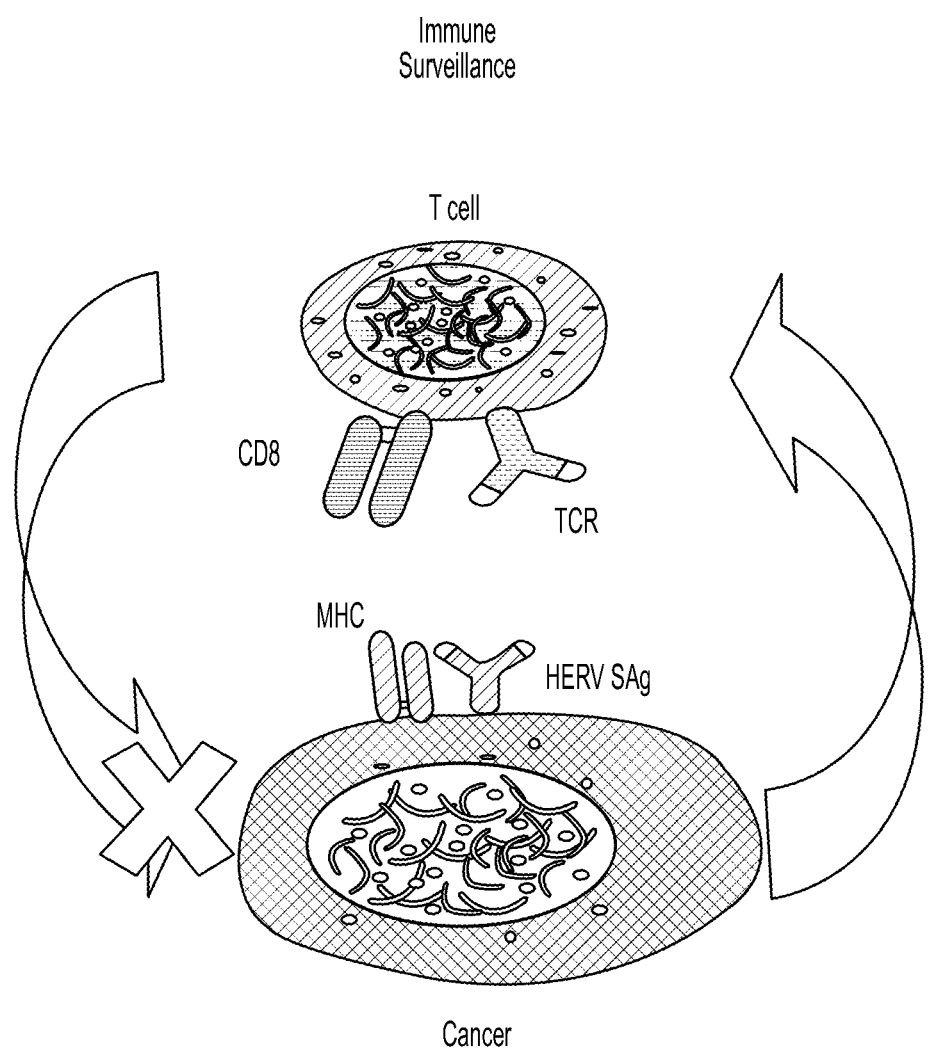
FIGS. 7A and 7B depicts immune surveillance vs. reverse immune surveillance.
Figure 7B:
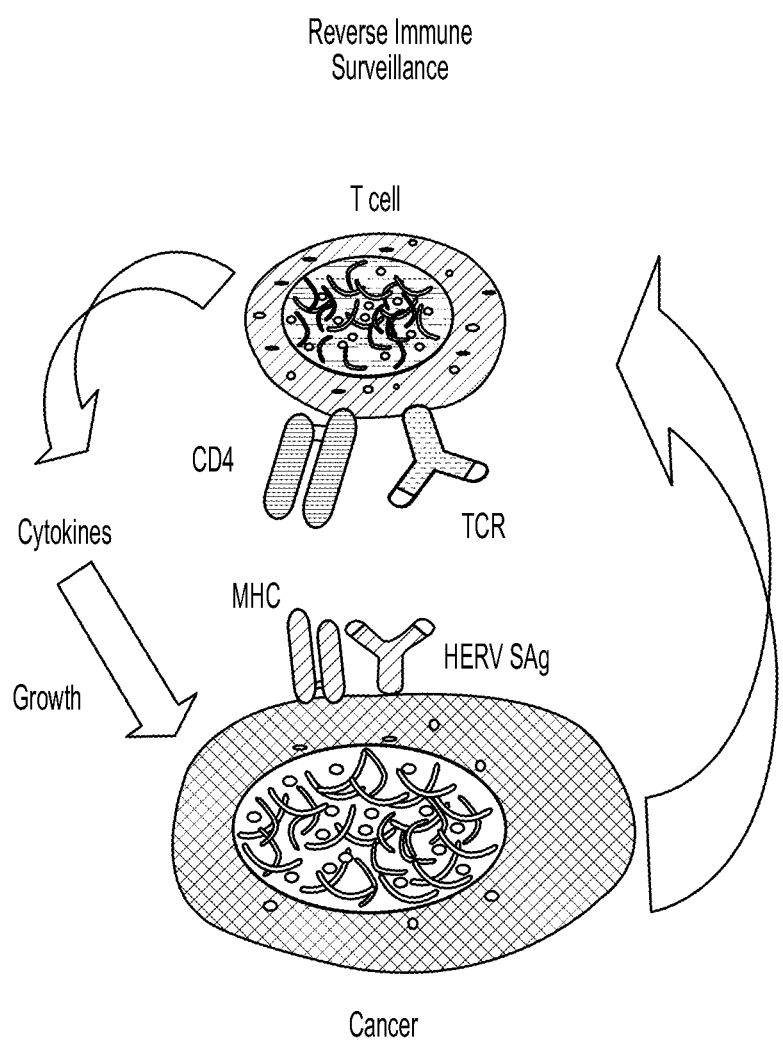

ELISA Detection of Human Endogenous Retroviral Protein HERV-WL in Saliva of Cancer Patients and Normal Individuals:

An explorative study was undertaken to examine saliva samples obtained from 9 cancer patients, at various stages between diagnosis and treatment. The hypothesis being tested WAS that endogenous retrovirus HERV-WL is over-expressed in saliva of some cancer patients, and such cancers may use this antigen in seeking help from host T cells for their growth—a process characterized as reverse immune surveillance, as illustrated in FIG. 7.

Saliva samples from cancer patients and from 5 normal healthy individuals were treated with protease inhibitors, and subjected to ELISA detection of HERV-WL protein by either anti-HERV-WL murine mAb or anti-HERV-WL rabbit polyclonal antisera, raised to SEQ ID NO: 2. Affinity purified murine monoclonal antibody to recombinant HERV-WL (murine anti-HERV-WL mAb) was produced. Recombinant HERV-WL protein was used to quantify the expression levels of the protein in saliva samples.

Figure 8:
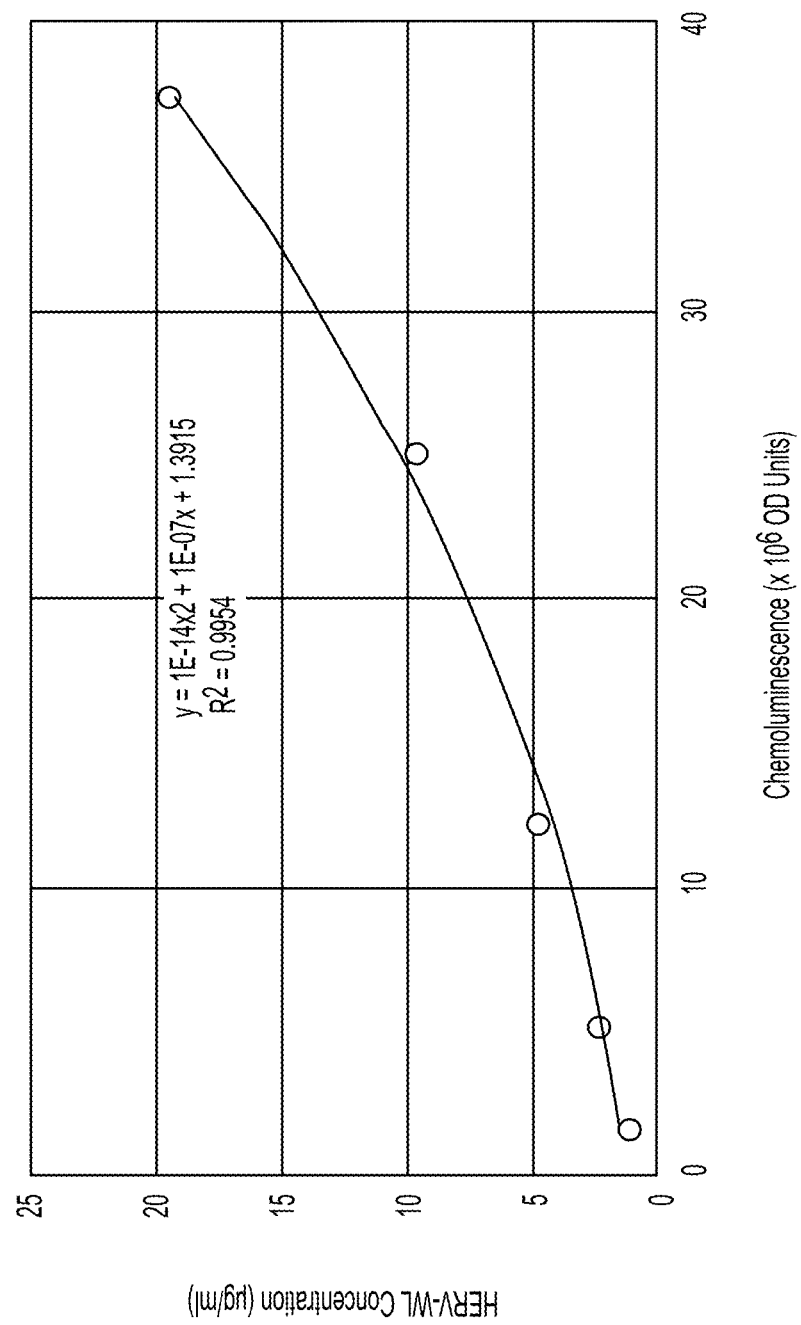
FIG. 8 depicts a standard curve of HERV-WL ELISA (monoclonal). Murine monoclonal anti-HERV-WL antibody was used to generate standard curve that was used to determine the concentration of HERV-WL in saliva of cancer patients and normal healthy individuals.

Saliva samples were obtained from University Hospital, and Oral Medicine clinic at RSDM (2 squamous cell carcinomas), and one with lymphoma. Saliva from cancer patients were compared with commercially acquired saliva from 5 normal subjects The samples were sonicated in the presence of protease inhibitors. Each sample was absorbed with NeutrAvidin Agarose resin to remove endogenous biotin. Duplicate serial two-fold dilutions of saliva, and standard recombinant HERV-WL protein, were coated in flat-bottomed 96-well plates at 4° C. overnight. Plates were blocked with StartingBlock™ T20 (TBS) blocking buffer at room temperature (RT) for 2 hours. Appropriate dilution of primary antibody (either murine anti-HERV-WL monoclonal antibody or rabbit anti-HERV-WL polyclonal antibody) was applied and the plates were incubated at RT for 2 hours. Secondary antibody (HRP labeled NeutrAvidin) was then coated, at appropriate dilution, and incubated at RT for 2 hours. Supersignal ELISA FemtoMax substrate was added and optical density was analyzed by chemoluminescence. Chemoluminescence optical density units were corrected for background prior to calculations. See FIG. 8 for standard curve of HERV-WL ELISA for the monoclonal antibody or FIG. 9 for standard curve of HERV-WL ELISA for the polyclonal antibody.

The results showed significantly higher HERV-WL protein expression in saliva samples from cancer patients, compared to saliva from normal healthy individuals. While HERV-wl protein expression was undetectable or less than 0.5 µg/mL in saliva from normal individuals, saliva from 7 out of 9 cancer patients showed HERV-WL protein expression levels ranging from 20-70 ug/ml. The expression patterns showed a gradation in various cancer patients at different stages. 2 of the 9 cancer patients who did not show detectable HERV-WL protein expression had received prior treatment. HERV-WL protein antigen concentration in saliva of normal and cancer patients is indicated in Tables 2 and 3 below.

TABLE 2

HERV-WL Concentration in saliva of normal and cancer patients (monoclonal antibody)

| Sample ID | Medical History | Mean HERV-WL concentration (µg./ml) |
|---|---|---|
| hNLSLV_1 | Normal healthy subject | 0.2 |
| hNLSLV_5 | Normal healthy subject | 0.3 |
| hNLSLV_2 | Normal healthy subject | undetectable |
| hNLSLV_3 | Normal healthy subject | undetectable |
| hNLSLV_4 | Normal healthy subject | undetectable |
| RSDM028 | Colon Cancer (Chemotherapy) | undetectable |
| RSDM029 | Squamous Cell Carcinoma (Chemotherapy and Radiotherapy) | undetectable |
| RSDM030 | Ameloblastoma (surgical resection) | 20 |
| RSDM032 | Squamous Cell Carcinoma (untreated) | 26 |
| RSDM033 | Squamous Cell Carcinoma (untreated) | 26 |
| RSDM034 | Squamous Cell Carcinoma (untreated) | 68 |
| RSDM035 | Throat Cancer (untreated) | 53 |
| RSDM036 | Squamous Cell Carcinoma (untreated) | 70 |

TABLE 3

HERV-WL Concentration in saliva of normal and cancer patients (polyclonal antibody)

| Sample ID | Medical History | Mean HERV-WL concentration (µg./ml) |
|---|---|---|
| hNLSLV_1 | Normal healthy subject | 0.2 |
| hNLSLV_5 | Normal healthy subject | 0.3 |
| hNLSLV_2 | Normal healthy subject | undetectable |
| hNLSLV_3 | Normal healthy subject | undetectable |
| hNLSLV_4 | Normal healthy subject | undetectable |
| RSDM024 | Lymphoma (on chemotherapy) | 4608 |
| RSDM025 | Squamous cell Carcinoma (untreated) | 2541 |
| RSDM027 | Squamous cell Carcinoma (untreated) | >12,000,000 |

HERV-WL is a Distinct Antigen from HERV-W

Cell lysate were prepared from Diffuse Large B cell lymphoma cell line (DB), which was shown to express of HERV-WL protein in the above Examples, using M-PER mammalian protein extraction reagent (Fisher), in presence of protease inhibitors. The lysates were run in gel electrophoresis, in duplicates, under reducing conditions, along with duplicates of chemiluminiscent SuperSignal Molecular Weight Protein ladder. The gel was blotted onto nitrocellulose using Iblot-2 dry transfer system. The nitrocellulose was cut into two, and individual blots were hybridized with either a. polyclonal anti-HERV-WL antibody that specifically bound to SEQ ID NO: 2, or b. commercially acquired anti-HERV-W antibody (ab71115 from Abcam) at 4° C.

overnight. The commercially acquired anti-HERV-W antibody was raised to amino acid residues 415-429 of HERV-W. This region of HERV-W overlaps with SEQ ID NO: 2, with the exception of one amino acid; the bold/underlined glycine in TEKVEIRDGIQRRA (SEQ ID NO: 2) was changed to an arginine (R). Horseradish peroxidase (HRP) conjugated goat anti-rabbit IgG (H+L) was used as a secondary antibody to detect the anti-HERV-WL and anti-HERV-W antibodies. The blots were developed using Super-Signal West Femto Maximum Sensitivity substrate (Fisher), and chemiluminiscence was read on Li-COR C-Digit blot scanner.

Figure 10B:
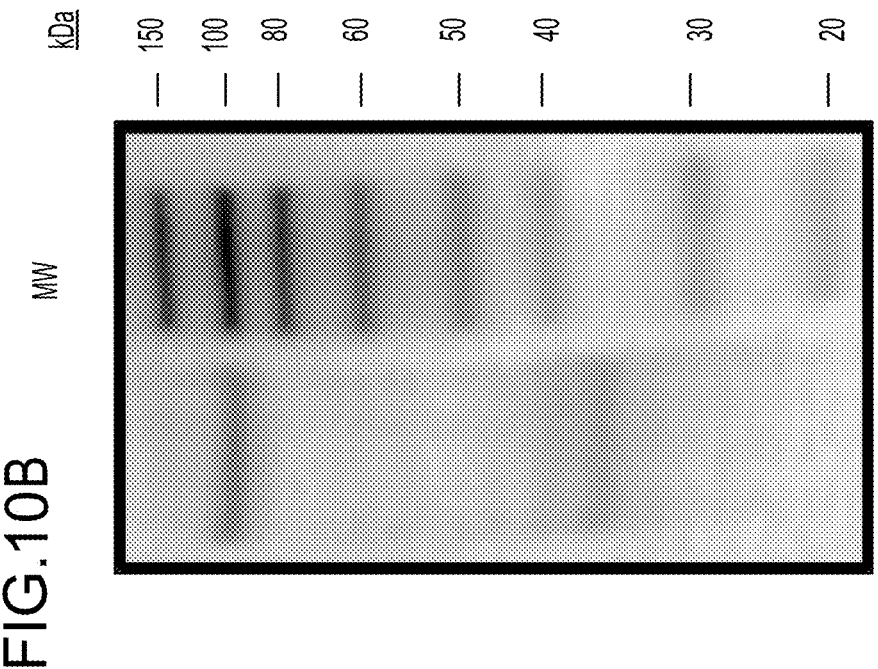
FIGS. 10A and 10B depicts the Western blot analysis of detection of HERV-WL and HERV-W.
Figure 10A:
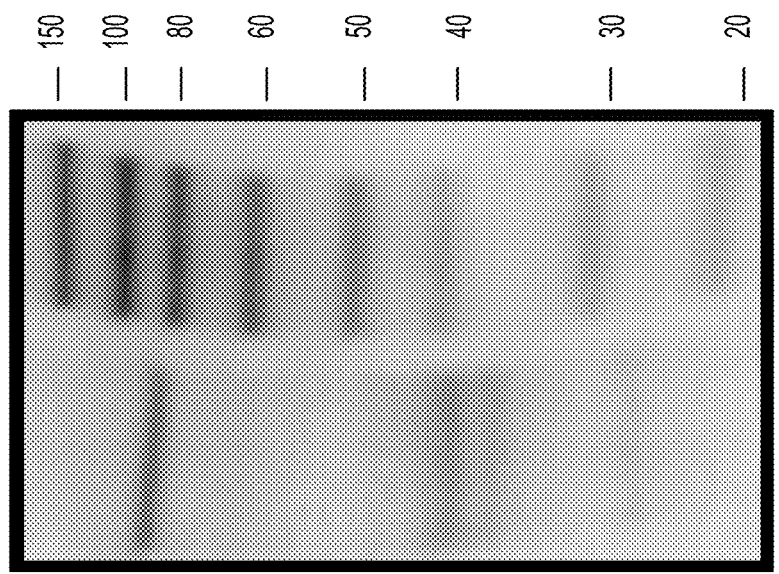

The results of the Western blot (FIG. 10) demonstrate that the anti-HERV-WL and anti-HERV-W antibodies recognize distinct proteins (HERV-W and HERV-WL) in the same cell. Thus, despite the similarity in amino acid sequence between SEQ ID NO: 2 and amino acid residues of 415-419 of HERV-W, the antibodies did not display cross-reactivity with one another. The anti-HERV-WL antibody recognized a 90 kDa protein (FIG. 10A), while the commercially available anti-HERV-W antibody recognized a 100 kDa protein (FIG. 10B) from the same cell lysate, in the same gel, under identical conditions. This experiment was repeated with identical results. This finding demonstrated that HERV-WL and HERV-W are distinct proteins from one another, irrespective of genetic relatedness.

Immunohistological Examination of HERV-WL Expression in Tissues from Papillomas

Figure 11:
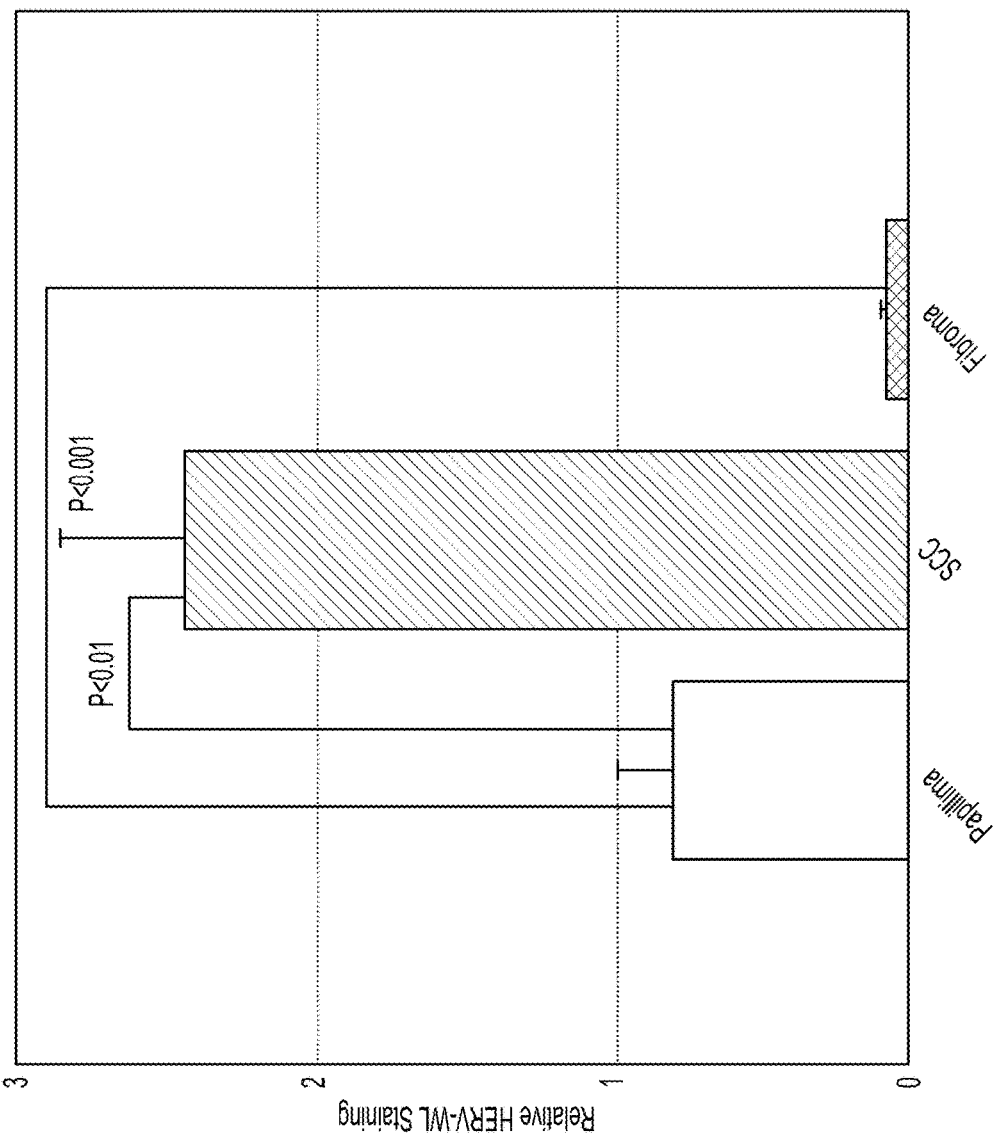
FIG. 11 depicts relative HERV-WL staining of tissues from papilloma (n=21), squamous cell carcinoma (SCC, n=10), and fibroma (n=10). 0=negative; 1=mild; 2=moderate; 3=intense. Values represent means±SEM. Using Student's t-test, staining scores of SCC vs. papilloma (PA) showed a statistically significant difference (p<0.01). The scores for PA and SCC were also significantly different from the score of fibroma (p<0.001).

Paraffin embedded tissue samples from papilloma lesions from 21 patients, and 10 squamous cell carcinoma patients (used as positive controls), were each run with anti-HERV-WL polyclonal antibody, raised to full-length HERV-WL env antigen, or with control normal rabbit IgG antibody. Ten samples of normal epithelium (fibroma), were used as negative controls. Sections of paraffin embedded tissue samples (coated on glass slides) were sequentially de-paraffinized and rehydrated in xylene followed by ethanol. This was followed by antigen retrieval in 0.1M citrate buffer (pH 6.0). Non-specific tissue binding was blocked using normal goat serum. This was followed by endogenous peroxidase block (3% hydrogen peroxide). Appropriately diluted rabbit polyclonal anti-HERV antibody or control normal rabbit IgG were applied to the slides, in Tris buffered saline (TBS). After extensive washes, Streptavidin HRP was applied to the slides, followed by washes and addition of diamino benzidine (DAB) chromogen substrate solution. The slides were counter-stained in Hematoxylin solution, and were mounted using Glycergel mounting medium. Staining results were evaluated independently by three previously calibrated investigators, ranking the epithelial staining according to a 0 (negative) to 3+ (intense) scale. Two-tailed Student's t-test was employed for determination of significance. Results are shown in FIG. 11.

All PA samples stained with anti-HERV IgG showed expression for HERV antigen in the epithelial component, ranging from mild to moderate. Samples of normal epithelium controls showed mild basal layer staining, but were otherwise negative for HERV antigen, while samples of squamous cell carcinoma were intensely positive. Tissue samples from papillomas showed mild to moderate staining with HERV-WL Ab, compared to a more intense staining of squamous cell carcinomas. These differences were statistically significant (p<0.01). HERV-WL staining scores in both papillomas and squamous cell carcinomas were significantly different from that of fibroma (p<0.001). Normal epithelium exhibits negligible staining with HERV-WL. No staining was observed with normal rabbit IgG in any of the tissues examined.

Immunohistological Examination of Pleomorphic Adenomas for HERV-WL Expression

Figure 12:
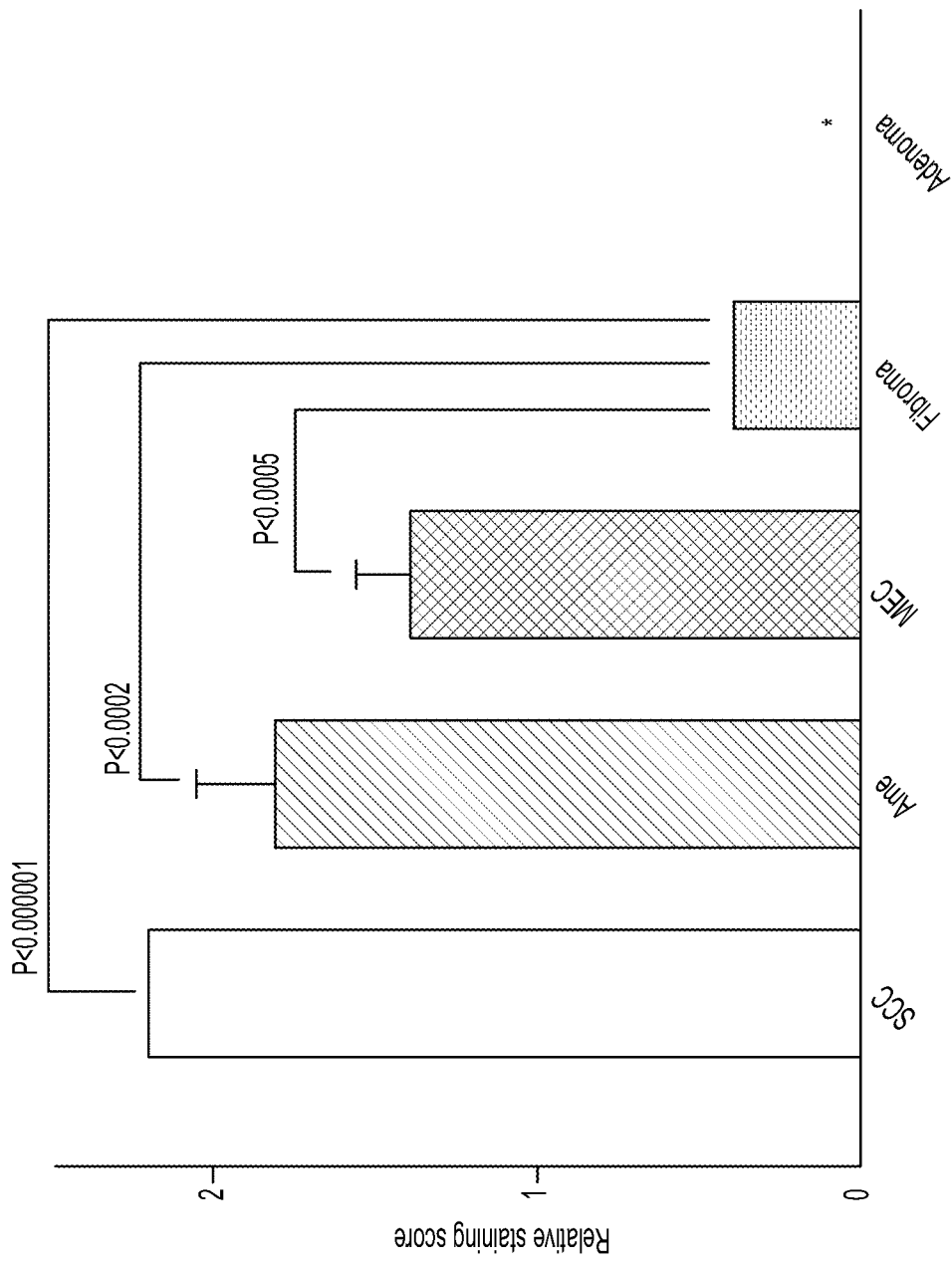
FIG. 12 depicts relative HERV-WL staining for tissues from squamous cell carcinoma (SCC, n=20), ameloblastoma (Ame, n=10), fibroma (n=10) and adenoma (n=10). Staining scores are as follows: 0=negative; 1=mild; 2=moderate; 3=intense. No staining was observed for all of the adenoma tissue samples. Values represent means±SEM, in comparison to mean fibroma score. Significance (p) values (in comparison to fibroma scores) were determined using Student's t-test.

Paraffin embedded tissue samples from 10 pleomorphic adenoma patients, 10 squamous cell carcinoma patients (used as positive controls), were each run with rabbit polyclonal anti-HERV-WL antibody, raised to full length HERV-WL env antigen, or with control normal rabbit IgG antibody. Ten samples of normal epithelium (fibroma), were used as negative controls. Sections of paraffin embedded tissue samples (coated on glass slides) were sequentially deparaffinized and rehydrated in xylene followed by ethanol. This was followed by antigen retrieval in 0.1M citrate buffer (pH 6.0). Non-specific tissue binding was blocked using normal goat serum. This was followed by endogenous peroxidase block (3% hydrogen peroxide). Appropriately diluted rabbit anti-HERV antibody or control normal rabbit IgG were applied to the slides, in Tris buffered saline (TBS). After extensive washes, Streptavidin HRP was applied to the slides, followed by washes and addition of diamino benzidine (DAB) chromogen substrate solution. The slides were counter-stained in Hematoxylin solution, and were mounted using Glycergel mounting medium. Staining results were evaluated independently by two previously calibrated investigators, ranking the epithelial staining according to a 0 (negative) to 3+ (intense) scale. Two-tailed Student's t-test was employed for determination of significance. Results are shown in FIG. 12.

Pleomorphic adenomas do not exhibit detectable HERV-WL expression, whereas oral squamous cell carcinomas, ameloblastomas and mucoepidermoid carcinomas exhibit strong HERV-WL expression. No staining was observed with normal rabbit IgG in any of the tissues examined. HERV-WL thus represents a tumor-associated antigen that is upregulated in squamous cell carcinomas, ameloblastomas and mucoepidermoid carcinomas, but not in benign pleomorphic adenomas or fibromas.

All publications, U.S. Patents and GenBank sequences cited in this disclosure are incorporated by reference in their entireties. The citation of any references herein is not an admission that such references are prior art to the present invention.

The embodiments within the specification provide an illustration of embodiments of the invention and should not be construed to limit the scope of the invention. The skilled artisan readily recognizes that many other embodiments are encompassed by the invention. Those skilled in the art will recognize, or be able to ascertain using no more than routine experimentation, many equivalents to the specific embodiments of the invention described herein. Such equivalents are intended to be encompassed by the following embodiments.

What is claimed is:

1. A method of detecting cancer cells in a subject comprising:
    a. obtaining a biological sample from said subject;
    b. detecting whether human endogenous retrovirus env (HERV-WL) is present in said biological sample by contacting the biological sample with an anti-HERV-WL-Env specific antibody that specifically binds to SEQ ID NO: 2, and detecting binding between HERV-WL-Env and the antibody;
    c. comparing the level of HERV-WL-Env detected in the biological sample to a standard level in a control sample; and
    d. wherein if the level of HERV-WL-Env is greater in the biological sample as compared to the standard level in the control sample, this greater level of HERV-WL-Env is indicative of cancer cells in the subject, wherein the cancer is one of: lymphoma, B cell lymphoma, non-Hodgkin's lymphoma, diffuse large B cell lymphoma, Burkitt's lymphoma, squamous cell carcinoma, mucoepidermoid carcinoma, cervical cancer, prostate cancer, ovarian cancer, ameloblastoma, throat cancer and breast cancer;
    wherein the anti-HERV-WL-Env specific antibody is a non-human, mammalian anti-HERV-WL-Env specific antibody.

2. The method of claim 1, wherein the anti-HERV-WL-Env specific antibody is a monoclonal antibody or antigen-binding fragment thereof.

3. The method of claim 1, wherein the anti-HERV-WL-Env specific antibody is a polyclonal antibody.

4. The method of claim 3, wherein the anti-HERV-WL-Env specific polyclonal antibody is created by immunizing one of a mouse, a pig, a goat, or a rabbit, with HERV-WL env.

5. The method of claim 3, wherein the anti-HERV-WL-Env specific polyclonal antibody is created by immunizing one of a mouse, a pig, a goat, or a rabbit, with a peptide consisting of SEQ ID NO: 2.

6. The method of claim 2, wherein the anti-HERV-WL-Env specific monoclonal antibody or antigen-binding fragment thereof is a murine antibody.

7. The method of claim 2, wherein the anti-HERV-WL-Env specific monoclonal antibody or antigen-binding fragment thereof is a F(ab')2 fragment.

8. The method of claim 1, wherein the biological sample comprises one of blood, plasma, serum, sputum, saliva, stool, tears, mucus, hair, and skin samples.

9. The method of claim 1, wherein the anti-HERV-WL-Env specific antibody is a polyclonal antibody or antigen-binding fragment thereof.

* * * * *

SEQUENCE LISTING

<160> NUMBER OF SEQ ID NOS: 17

<210> SEQ ID NO 1

<211> LENGTH: 1617
<212> TYPE: DNA
<213> ORGANISM: Homo sapiens

<400> SEQUENCE: 1

```
atggccctcc cttatcatat ttttctcttt actgttctct tacccccttt cattctcact      60
gcaccccctc catgccactg tatgaccagt agctcccgtt accaagagtt tctatggaga     120
atgcggcttc ccggaaatat tgatgcccca tcatatagga gtttatctaa gggaaacccc     180
accttcactg cccataccca tgccccgc aactgctgta actctgccac tctttgcatg      240
catgcaaata tcattattg acagggaaa attttaatc ctagttgtcc gggaggactt       300
ggagccactg tctgttggac ttacttcacc cataccagta tgtctgatgg gcgtggagtt    360
caagatcagg caggagaaaa acacataaag gaagtaatct cccaactgac ccgggtacat    420
agcaccccta accctacaa aggactagat ctctcaaaac tacatgaaac cctccatacc     480
catactcacc aggtaagcct atttaatacc cccctcactg ggctccatga ggccttggcc    540
caaaaccccta ctaactgttg aatgtgcctc cccctgcact acaggccaca tatttcaatc   600
cctgtacctg aacaatggaa caacttcagc acagaaataa acaccacttc cattttagta    660
ggacctcttg tttccaatct ggaaataacc catacctcaa acctcgcccg tgtaaaattt    720
agcaatacta tagacacaac caactcccag tgcatcagat gggtaactcc tcccacacaa    780
atagtctgcc tacctcagg aatattttt gtctgtggta cctcagccta tcactgtttg     840
aatggctttt cggaatctat gtgcttcctc tcattcttag tgcaccctat gaccatctac    900
actgaacaag atttatacaa ttatgtcgta cctaagcccc gcaacaaaag agtacccatt    960
cttccttttg ttatccgagc aggaatgcta ggcagattag gtactggcat gggcagtatc   1020
acaacctcta ctcagttcta ctacaaacta tctcaagaac taaatggtga catggaacgg   1080
gttgccgact ccctggtcac cttgcaagat caacttaact ccctagcagc agtagtactt   1140
caaaatcgaa gagctttaga cttgctaact gcagaaagag ggggaacctg ttttatttta   1200
ggggaagaat gctgttatta tgttaatcaa tctggaatca tcactgagaa agttaaagaa   1260
attcgagatg gaatacaacg cagagcatag gagcttcaaa gcaccagacc ctggggcctc   1320
ctcagccagt ggatgccctg gattctcccc ttcttaggac ctctagcagc tataatattg   1380
ttactcttct ttggaccctg tacctttaac ctccttatta aattggtctc ttccagaatc   1440
gaagcggtaa agctacaaat ggagccccag atgcagtcca tgactaaaat ctaccacaga   1500
cccctggacc agcctgctag cccatgctct gatgttgatg acactgaagt cacccctccc   1560
gaggaaatct caactgcatg acccctacta tgccccaatt cagcaggaag cagttag      1617
```

<210> SEQ ID NO 2
<211> LENGTH: 15
<212> TYPE: PRT
<213> ORGANISM: Homo sapiens

<400> SEQUENCE: 2

```
Thr Glu Lys Val Lys Glu Ile Arg Asp Gly Ile Gln Arg Arg Ala
1               5                   10                  15
```

<210> SEQ ID NO 3
<211> LENGTH: 20
<212> TYPE: DNA
<213> ORGANISM: Artificial Sequence
<220> FEATURE:
<223> OTHER INFORMATION: Primer

```
<400> SEQUENCE: 3
cttagtgccc cctatgacca                                              20

<210> SEQ ID NO 4
<211> LENGTH: 20
<212> TYPE: DNA
<213> ORGANISM: Artificial Sequence
<220> FEATURE:
<223> OTHER INFORMATION: Primer

<400> SEQUENCE: 4
cgccaatgcc agtacctagt                                              20

<210> SEQ ID NO 5
<211> LENGTH: 22
<212> TYPE: DNA
<213> ORGANISM: Artificial Sequence
<220> FEATURE:
<223> OTHER INFORMATION: Primer

<400> SEQUENCE: 5
aacaacagcc tgccacctta cg                                           22

<210> SEQ ID NO 6
<211> LENGTH: 22
<212> TYPE: DNA
<213> ORGANISM: Artificial Sequence
<220> FEATURE:
<223> OTHER INFORMATION: Primer

<400> SEQUENCE: 6
gctgctgcct ttgttgctct tc                                           22

<210> SEQ ID NO 7
<211> LENGTH: 18
<212> TYPE: DNA
<213> ORGANISM: Artificial Sequence
<220> FEATURE:
<223> OTHER INFORMATION: Primer

<400> SEQUENCE: 7
atggccctcc cttatcat                                                18

<210> SEQ ID NO 8
<211> LENGTH: 18
<212> TYPE: DNA
<213> ORGANISM: Artificial Sequence
<220> FEATURE:
<223> OTHER INFORMATION: Primer

<400> SEQUENCE: 8
ctaactgctt cctgctga                                                18

<210> SEQ ID NO 9
<211> LENGTH: 27
<212> TYPE: DNA
<213> ORGANISM: Artificial Sequence
<220> FEATURE:
<223> OTHER INFORMATION: Primer

<400> SEQUENCE: 9
aactcttcaa tggccctccc ttatcat                                      27

<210> SEQ ID NO 10
<211> LENGTH: 18
```

<210> SEQ ID NO 10
<211> LENGTH: 18
<212> TYPE: DNA
<213> ORGANISM: Artificial Sequence
<220> FEATURE:
<223> OTHER INFORMATION: Primer

<400> SEQUENCE: 10
ctaactgctt cctgctga                                                 18

<210> SEQ ID NO 11
<211> LENGTH: 26
<212> TYPE: DNA
<213> ORGANISM: Artificial Sequence
<220> FEATURE:
<223> OTHER INFORMATION: Primer

<400> SEQUENCE: 11
tagaattcat ggccctccct tatcat                                        26

<210> SEQ ID NO 12
<211> LENGTH: 26
<212> TYPE: DNA
<213> ORGANISM: Artificial Sequence
<220> FEATURE:
<223> OTHER INFORMATION: Primer

<400> SEQUENCE: 12
aagtcgacct aactgcttcc tgctga                                        26

<210> SEQ ID NO 13
<211> LENGTH: 561
<212> TYPE: DNA
<213> ORGANISM: homo sapiens

<400> SEQUENCE: 13
atggccctcc cttatcatat ttttctcttt actgttctct taccccttt cattctcact      60 gcaccccctc catgccactg tatgaccagt agctcccgtt accaagagtt cattggaga     120 atgcggcttc ccggaaataa tgatgcccca tcatatagga gtttatctaa gggaaacccc    180
accttcactg cccataccca tatgccccgc acctgctgta actctgccac tctttgcatg    240
catgcaaata ctcattattg gacagggaaa attttaatc ctagttgtcc gggaggactt     300
ggagccactg tctgttggac ttacttcacc cataccagta tgtctgatgg cgtggagtt     360 caagatcagg caggagaaaa acacataaag gaagtaatct cccaactgac ccgggtacat    420
agcaccccta ccccctacaa aggactagat ctctcaaaac tacatgaaac cctccatacc    480
catactcacc aggtaagcct atttaatacc accctcactg ggctccatga ggccttggcc    540
caaaacccta ctaactgttg a                                             561

<210> SEQ ID NO 14
<211> LENGTH: 186
<212> TYPE: PRT
<213> ORGANISM: homo sapiens

<400> SEQUENCE: 14

Met Ala Leu Pro Tyr His Ile Phe Leu Phe Thr Val Leu Leu Pro Pro
1               5                   10                  15

Phe Ile Leu Thr Ala Pro Pro Cys His Cys Met Thr Ser Ser Ser
            20                  25                  30

Arg Tyr Gln Glu Phe Leu Trp Arg Met Arg Leu Pro Gly Asn Ile Asp
        35                  40                  45

Ala Pro Ser Tyr Arg Ser Leu Ser Lys Gly Asn Pro Thr Phe Thr Ala

```
            50                  55                  60
His Thr His Met Pro Arg Asn Cys Cys Asn Ser Ala Thr Leu Cys Met
 65                  70                  75                  80

His Ala Asn Thr His Tyr Trp Thr Gly Lys Ile Phe Asn Pro Ser Cys
                 85                  90                  95

Pro Gly Gly Leu Gly Ala Thr Val Cys Trp Thr Tyr Phe Thr His Thr
            100                 105                 110

Ser Met Ser Asp Gly Arg Gly Val Gln Asp Gln Ala Gly Glu Lys His
        115                 120                 125

Ile Lys Glu Val Ile Ser Gln Leu Thr Arg Val His Ser Thr Pro Asn
130                 135                 140

Pro Tyr Lys Gly Leu Asp Leu Ser Lys Leu His Glu Thr Leu His Thr
145                 150                 155                 160

His Thr His Gln Val Ser Leu Phe Asn Thr Thr Leu Thr Gly Leu His
                165                 170                 175

Glu Ala Leu Ala Gln Asn Pro Thr Asn Cys
            180                 185

<210> SEQ ID NO 15
<211> LENGTH: 729
<212> TYPE: DNA
<213> ORGANISM: homo sapiens

<400> SEQUENCE: 15
atgtgcctcc ccctgcacta caggccacat atttcaatcc ctgtacctga caatggaac      60
aacttcagca cagaaataaa caccacttcc attttagtag gacctcttgt ttccaatctg    120
gaaataaccc atacctcaaa cctcgcccgt gtaaaattta gcaatactat agacacaacc    180
aactcccagt gcatcagatg ggtaactcct cccacacaaa tagtctgcct accctcagga    240
atatttttg tctgtggtac ctcagcctat cactgtttga atggcttttc ggaatctatg    300
tgcttcctct cattcttagt gcaccctatg accatctaca ctgaacaaga tttatacaat    360
tatgtcgtac ctaagcccg caacaaaaga gtacccattc ttccttttgt tatccgagca    420
ggaatgctag gcagattagg tactggcatg gcagtatca caacctctac tcagttctac    480
tacaaactat ctcaagaact aaatggtgac atggaacggg ttgccgactc cctggtcacc    540
ttgcaagatc aacttaactc cctagcagca gtagtacttc aaaatcgaag agctttagac    600
ttgctaactg cagaaagagg gggaaccctgt ttattttag gggaagaatg ctgttattat    660
gttaatcaat ctggaatcat cactgagaaa gttaagaaa ttcgagatgg aatacaacgc    720
agagcatag                                                            729

<210> SEQ ID NO 16
<211> LENGTH: 242
<212> TYPE: PRT
<213> ORGANISM: homo sapiens

<400> SEQUENCE: 16

Met Cys Leu Pro Leu His Tyr Arg Pro His Ile Ser Ile Pro Val Pro
  1               5                  10                  15

Glu Gln Trp Asn Asn Phe Ser Thr Glu Ile Asn Thr Thr Ser Ile Leu
             20                  25                  30

Val Gly Pro Leu Val Ser Asn Leu Glu Ile Thr His Thr Ser Asn Leu
         35                  40                  45

Ala Arg Val Lys Phe Ser Asn Thr Ile Asp Thr Thr Asn Ser Gln Cys
     50                  55                  60
```

```
Ile Arg Trp Val Thr Pro Pro Thr Gln Ile Val Cys Leu Pro Ser Gly
 65                  70                  75                  80

Ile Phe Phe Val Cys Gly Thr Ser Ala Tyr His Cys Leu Asn Gly Phe
                 85                  90                  95

Ser Glu Ser Met Cys Phe Leu Ser Phe Leu Val His Pro Met Thr Ile
            100                 105                 110

Tyr Thr Glu Gln Asp Leu Tyr Asn Tyr Val Val Pro Lys Pro Arg Asn
        115                 120                 125

Lys Arg Val Pro Ile Leu Pro Phe Val Ile Arg Ala Gly Met Leu Gly
130                 135                 140

Arg Leu Gly Thr Gly Met Gly Ser Ile Thr Thr Ser Thr Gln Phe Tyr
145                 150                 155                 160

Tyr Lys Leu Ser Gln Glu Leu Asn Gly Asp Met Glu Arg Val Ala Asp
                165                 170                 175

Ser Leu Val Thr Leu Gln Asp Gln Leu Asn Ser Leu Ala Ala Val Val
            180                 185                 190

Leu Gln Asn Arg Arg Ala Leu Asp Leu Leu Thr Ala Glu Arg Gly Gly
        195                 200                 205

Thr Cys Phe Leu Phe Gly Glu Glu Cys Cys Tyr Tyr Val Asn Gln Ser
210                 215                 220

Gly Ile Ile Thr Glu Lys Val Lys Glu Ile Arg Gly Asp Ile Gln Arg
225                 230                 235                 240

Arg Ala

<210> SEQ ID NO 17
<211> LENGTH: 428
<212> TYPE: PRT
<213> ORGANISM: homo sapiens

<400> SEQUENCE: 17

Met Ala Leu Pro Tyr His Ile Phe Leu Phe Thr Val Leu Leu Pro Pro
  1               5                  10                  15

Phe Ile Leu Thr Ala Pro Pro Cys His Cys Met Thr Ser Ser Ser Ser
                 20                  25                  30

Arg Tyr Gln Glu Phe Leu Trp Arg Met Arg Leu Pro Gly Asn Ile Asp
            35                  40                  45

Ala Pro Ser Tyr Arg Ser Leu Ser Lys Gly Asn Pro Thr Phe Thr Ala
         50                 55                  60

His Thr His Met Pro Arg Asn Cys Cys Asn Ser Ala Thr Leu Cys Met
 65                  70                  75                  80

His Ala Asn Thr His Tyr Trp Thr Gly Lys Ile Phe Asn Pro Ser Cys
                 85                  90                  95

Pro Gly Gly Leu Gly Ala Thr Val Cys Trp Thr Tyr Phe Thr His Thr
            100                 105                 110

Ser Met Ser Asp Gly Arg Gly Val Gln Asp Gln Ala Gly Glu Lys His
        115                 120                 125

Ile Lys Glu Val Ile Ser Gln Leu Thr Arg Val His Ser Thr Pro Asn
130                 135                 140

Pro Tyr Lys Gly Leu Asp Leu Ser Lys Leu His Glu Thr Leu His Thr
145                 150                 155                 160

His Thr His Gln Val Ser Leu Phe Asn Thr Thr Leu Thr Gly Leu His
                165                 170                 175

Glu Ala Leu Ala Gln Asn Pro Thr Asn Cys Met Cys Leu Pro Leu His
            180                 185                 190
```

```
Tyr Arg Pro His Ile Ser Ile Pro Val Pro Glu Gln Trp Asn Asn Phe
        195             200             205

Ser Thr Glu Ile Asn Thr Thr Ser Ile Leu Val Gly Pro Leu Val Ser
        210             215             220

Asn Leu Glu Ile Thr His Thr Ser Asn Leu Ala Arg Val Lys Phe Ser
225             230             235             240

Asn Thr Ile Asp Thr Thr Asn Ser Gln Cys Ile Arg Trp Val Thr Pro
            245             250             255

Pro Thr Gln Ile Val Cys Leu Pro Ser Gly Ile Phe Phe Val Cys Gly
            260             265             270

Thr Ser Ala Tyr His Cys Leu Asn Gly Phe Ser Glu Ser Met Cys Phe
        275             280             285

Leu Ser Phe Leu Val His Pro Met Thr Ile Tyr Thr Glu Gln Asp Leu
        290             295             300

Tyr Asn Tyr Val Val Pro Lys Pro Arg Asn Lys Arg Val Pro Ile Leu
305             310             315             320

Pro Phe Val Ile Arg Ala Gly Met Leu Gly Arg Leu Gly Thr Gly Met
                325             330             335

Gly Ser Ile Thr Thr Ser Thr Gln Phe Tyr Tyr Lys Leu Ser Gln Glu
            340             345             350

Leu Asn Gly Asp Met Glu Arg Val Ala Asp Ser Leu Val Thr Leu Gln
            355             360             365

Asp Gln Leu Asn Ser Leu Ala Ala Val Val Leu Gln Asn Arg Arg Ala
        370             375             380

Leu Asp Leu Leu Thr Ala Glu Arg Gly Gly Thr Cys Phe Leu Phe Gly
385             390             395             400

Glu Glu Cys Cys Tyr Tyr Val Asn Gln Ser Gly Ile Ile Thr Glu Lys
            405             410             415

Val Lys Glu Ile Arg Gly Asp Ile Gln Arg Arg Ala
            420             425
```